(12) United States Patent
Zemek et al.

(10) Patent No.: US 10,228,324 B2
(45) Date of Patent: Mar. 12, 2019

(54) GAS MEASUREMENT SYSTEM

(71) Applicant: MKS Instruments, Inc., Andover, MA (US)

(72) Inventors: Peter Zemek, Groton, MA (US); Robert M. Carangelo, Glastonbury, CT (US); Hongke Ye, Chelmsford, MA (US); Andrew Wright, North Andover, MA (US)

(73) Assignee: MKS Instruments, Inc., Andover, MA (US)

( * ) Notice: Subject to any disclaimer, the term of this patent is extended or adjusted under 35 U.S.C. 154(b) by 0 days.

(21) Appl. No.: 15/658,470

(22) Filed: Jul. 25, 2017

(65) Prior Publication Data

US 2018/0024051 A1    Jan. 25, 2018

Related U.S. Application Data

(60) Provisional application No. 62/366,594, filed on Jul. 25, 2016.

(51) Int. Cl.
*G01N 21/39* (2006.01)
*G01N 21/01* (2006.01)
(Continued)

(52) U.S. Cl.
CPC ............ *G01N 21/39* (2013.01); *G01N 21/01* (2013.01); *G01N 21/255* (2013.01);
(Continued)

(58) Field of Classification Search
CPC .... G01N 21/39; G01N 21/01; G01N 33/0044; G01N 2021/399; G01N 2021/0193; G01N 2201/129; G01N 2201/0612
See application file for complete search history.

(56) References Cited

U.S. PATENT DOCUMENTS 5,528,040 A * 6/1996 Lehmann ............... G01J 3/42
250/343
6,248,078 B1    6/2001 Risby et al.
(Continued)

OTHER PUBLICATIONS

International Search Report, PCT/US2017/043588 (Gas Measurement System, filed Jul. 25, 2017), issued by ISA/KR Office, dated Nov. 9, 2017, 4 pages.
(Continued)

*Primary Examiner* — Sang H Nguyen
(74) *Attorney, Agent, or Firm* — Choate, Hall & Stewart LLP; William R. Haulbrook; Margo R. Monroe

(57) ABSTRACT

Presented herein are systems and methods for quantifying trace and/or ultra-trace levels of a species—for example, $H_2S$ or $H_2O$—in a natural gas line. The systems and methods employ a tunable laser, such as a tunable diode laser, vertical-cavity surface-emitting laser (VCSEL), external cavity diode laser or a vertical external-cavity surface-emitting laser (VECSEL) or a tunable quantum cascade laser (QCL). The laser produces an output beam over a set of one or more relatively narrow, high resolution wavelength bands at a scan rate from about 0.1 Hz to about 1000 Hz. A natural gas sample comprising a trace level of a species of interest passes through a flow cell into which the output beam from the laser is guided. An optical detector receives light from the flow cell, producing a signal indicative of the absorption attenuation from which the concentration of the trace species is determined.

24 Claims, 13 Drawing Sheets

(51) Int. Cl.
*G01N 33/00* (2006.01)
*G01N 21/25* (2006.01)

(52) U.S. Cl.
CPC . *G01N 33/0044* (2013.01); *G01N 2021/0193* (2013.01); *G01N 2021/399* (2013.01); *G01N 2201/0612* (2013.01); *G01N 2201/129* (2013.01)

(56) References Cited

U.S. PATENT DOCUMENTS

| | | | |
|---|---|---|---|
| 6,421,127 B1 | 7/2002 | McAndrew et al. | |
| 6,657,198 B1 | 12/2003 | May | |
| 6,741,348 B2 | 5/2004 | Larsen et al. | |
| 7,132,661 B2 | 11/2006 | May | |
| 7,192,782 B2 | 3/2007 | Roller et al. | |
| 7,262,844 B2 | 8/2007 | Larsen et al. | |
| 7,339,168 B2 | 3/2008 | May | |
| 7,352,463 B2 | 4/2008 | Bounaix | |
| 7,504,631 B2 | 3/2009 | May | |
| 7,616,316 B1 * | 11/2009 | Silver | G01N 21/39 356/409 |
| 7,704,301 B2 | 4/2010 | Zhou et al. | |
| 7,710,568 B1 | 5/2010 | Paige et al. | |
| 7,903,252 B2 | 3/2011 | Larsen et al. | |
| 8,063,373 B2 | 11/2011 | Miller | |
| 8,327,686 B2 * | 12/2012 | Kachanov | G01N 21/1702 250/339.13 |
| 8,547,554 B2 | 10/2013 | Liu et al. | |
| 8,664,004 B2 | 3/2014 | Spiegelman et al. | |
| 8,686,364 B1 | 4/2014 | Little, III et al. | |
| 2003/0189711 A1 * | 10/2003 | Orr | G01J 3/42 356/484 |
| 2007/0064748 A1 * | 3/2007 | Mirov | C30B 31/00 372/20 |
| 2008/0135760 A1 * | 6/2008 | May | G01N 21/3504 250/338.5 |
| 2008/0179530 A1 | 7/2008 | Liu et al. | |
| 2011/0027803 A1 | 2/2011 | Moussavi et al. | |
| 2011/0032516 A1 * | 2/2011 | Zhou | G01N 21/39 356/73 |
| 2011/0213554 A1 | 9/2011 | Archibald et al. | |
| 2013/0003045 A1 | 1/2013 | Wilkins | |
| 2013/0056626 A1 | 3/2013 | Shen et al. | |
| 2014/0204382 A1 | 7/2014 | Christensen | |
| 2014/0260708 A1 | 9/2014 | Harrell et al. | |
| 2014/0293283 A1 * | 10/2014 | Farooq | G01N 33/0054 356/437 |
| 2014/0361172 A1 | 12/2014 | Little, III et al. | |
| 2014/0370607 A1 | 12/2014 | Dimick et al. | |
| 2014/0373649 A1 | 12/2014 | Harrell et al. | |
| 2015/0047712 A1 | 2/2015 | Little, III et al. | |
| 2015/0377774 A1 | 12/2015 | Saptari | |
| 2017/0199126 A1 * | 7/2017 | Jena | G01N 21/6489 |

OTHER PUBLICATIONS

Written Opinion, PCT/US2017/043588 (Gas Measurement System, filed Jul. 25, 2017), issued by ISA/KR Office, dated Nov. 9, 2017, 11 pages.

* cited by examiner

GAS MEASUREMENT SYSTEM

CROSS REFERENCE TO RELATED APPLICATION

This application claims the benefit of U.S. Application Ser. No. 62/366,594 filed on Jul. 25, 2016, the disclosure of which is hereby incorporated by reference in its entirety.

FIELD

The invention relates generally to systems and methods for detecting and measuring gases in a sample. More particularly, in certain embodiments, the invention relates to absorption spectroscopy systems and methods for quantifying a rare species (e.g., hydrogen sulfide) in a gas sample, e.g., a natural gas sample.

BACKGROUND

Natural gas has become more important for industries, such as power generation, to meet more stringent regulatory constraints, and provide cleaner alternatives to reduce equipment maintenance and service. As more infrastructure and fracking well supplies proliferate in the US and overseas markets, reliable traditional natural gas reserves are being mixed or replaced with natural gas supplies with more physical make-up variability. Natural gas supplies are becoming more readily available. Distribution sites and associated infrastructure, like ports, make products like compressed natural gas (CNG) and liquefied natural gas (LNG) more readily available to replace other fossil fuels such as coal and oil. However, as these traditional and new sources are mixed in pipelines and into saleable product, mixtures are becoming more varied and require more accurate and higher temporal resolution in continuous testing for undesirable contaminants if the company is going to meet consumer expectations.

Natural gas is composed primarily of methane ($CH_4$) and hydrocarbon gases and contaminants such as carbon dioxide ($CO_2$), nitrogen ($N_2$), hydrogen sulfide ($H_2S$) and water ($H_2O$). As more sources of fracking gas come on-line and industries convert to cleaner burning fuels like CNG, the composition of CNG is more varied and includes species like sulfur compounds which may cause corrosion and performance issues.

The presence of sulfur in its most common reduced form in natural gas is as hydrogen sulfide ($H_2S$). The hydrogen sulfide molecule consists of two hydrogen atoms bonded to a single sulfur atom. Its molecular composition is similar to that of water ($H_2O$), two hydrogen atoms bonded to a single oxygen atom. Because sulfur can substitute as an oxidizer in place of oxygen, $H_2S$ is easily produced in anaerobic environments from the sulfur left over from decayed organic matter such as is found in fossil fuels. $H_2S$ is generally found in higher concentrations in fracking gas due to the association of the natural gas and $H_2S$ in the interstices of porous material where fracking gas is obtained. Fracking involves the recovery of shale gas which is natural gas that is trapped within layers and pores of rock formations or boundary layers. The fracking boom of the early 2000's has resulted in a variety of gas sources that differ in quality and physical characteristics such as sulfur content. Natural gas is considered "sour" if it has a high percentage of hydrogen sulfide. It has been estimated that 15 to 25% of natural gas in the U.S. may contain hydrogen sulfide at part per million by volume (ppmv) levels.

Energy companies must ensure that gas feeds from fracking meet quality industry standards before distributing to its customers. A fast and ultra-sensitive instrument for measuring $H_2S$ content is critical to the efficiency and cost effectiveness of these operations. Additionally, when one company sells or transfers gas to another company such as from a fracking site to a pipeline company, it is called a "custody transfer point." At this point where the gas is transferred, the gas purchaser must measure hydrogen sulfide concentration or risk pipeline damage or damage to equipment at a downstream customer or consumer location. In most natural gas supply agreements, The Federal Energy Regulatory Commission (FERC) requires that pipeline gas contain hydrogen sulfide in amounts less than 4 PPM/V. Most custody transfer contracts also specify this limit.

Water is also found in natural gas and may be more concentrated in fracking gas due also to the association with the interstices in porous material and the need to inject large quantities of water in the fracking process. When water combines with carbon dioxide and hydrogen sulfide it forms carbonic and sulfuric acids which are very corrosive to metals. The acids can quickly break down metal pipes, tanks, or other metal materials with which they come into contact. The corrosive nature of $H_2S$ can cause pipes or tanks to develop leaks or weaken the structure, causing failure.

Thus, there is a need for an improved method and system for monitoring hydrogen sulfide, water, or other trace species in natural gas.

SUMMARY

Presented herein are systems and methods for quantifying trace and/or ultra-trace levels of a species—for example, $H_2S$ or $H_2O$—in a natural gas line. The systems and methods employ a tunable laser, such as a tunable diode laser (e.g., distributed feedback laser (DFB), vertical-cavity surface-emitting laser (VCSEL), external cavity diode laser or a vertical external-cavity surface-emitting laser (VECSEL) or a tunable quantum cascade laser (QCL). The laser produces an output beam over a relatively (e.g., very) narrow (or "high resolution") wavelength band whose center can be continuously or discretely scanned from about 0.1 Hz to about 1000 Hz. A natural gas sample comprising a trace level of a species of interest (e.g., $H_2S$ or $H_2O$) passes through a flow cell into which the output beam from the laser is guided. An optical detector receives light from the flow cell, producing a signal indicative of the absorption attenuation from which the concentration of the trace species is determined (e.g., via chemometric analysis of the generated absorption spectrum in the time or frequency domain).

In one aspect, the invention is directed to a spectroscopy system [e.g., a tunable diode laser absorption spectroscopy (TDLAS system) or a tunable quantum cascade laser (QCL) system] for measuring a trace level (e.g., no greater than 1000 ppm, e.g., no greater than 500 ppm, e.g., no greater than 250 ppm, e.g., no greater than 200 ppm, e.g., no greater than 100 ppm, e.g., no greater than 50 ppm, e.g., no greater than 25 ppm, e.g., no greater than 10 ppm, e.g., no greater than 5 ppm, e.g., no greater than 2 ppm, e.g., no greater than 1 ppm) and/or an ultra-trace level (e.g., less than 1 ppm, e.g., less than 500 ppb, e.g., less than 250 ppb, e.g., less than 100 ppb, e.g., less than 50 ppb, e.g., less than 25 ppb, e.g., less than 10 ppb, e.g., less than 5 ppb, e.g., less than 2 ppb, e.g., less than 1 ppb) of a first gas (e.g., hydrogen sulfide or $H_2O$) in a natural gas sample, the system comprising: a laser [e.g., a tunable diode laser, such as a distributed feedback laser (DFB), a vertical-cavity surface-emitting laser (VCSEL), an external cavity diode laser or a vertical external-cavity surface-emitting laser (VECSEL)] [e.g., a tunable quantum cascade laser (QCL)] for producing an output beam over a set of one or more discrete or continuous wavelength bands at a scan rate from about 0.1 Hz to about 1000 Hz over the set of one or more discrete or continuous wavelength bands [e.g., at a resolution of from 0.01 to 0.0001 cm$^{-1}$, e.g., at an ultra-high resolution, e.g., at a resolution of 0.001 cm$^{-1}$ or lower (/better)]; transmitting optics for guiding and/or shaping the output beam from the tunable diode laser to the natural gas sample [e.g., guiding and/or shaping the beam to a flow cell (e.g., a multi-pass cell) through which the natural gas sample flows, e.g., wherein the natural gas sample is an absorbing medium]; an optical detector (e.g., a photodiode or other fast response detector) for receiving light from the natural gas sample and producing a detector signal corresponding to the received light (e.g., said received light having been transmitted through and/or reflected from transfer optics located between the natural gas sample and the optical detector); and a processor of a computing device and a memory (non-transitory computer-readable medium) having instructions stored thereon, wherein the instructions, when executed by the processor, cause the processor to compute the trace level (e.g., no greater than 1000 ppm, e.g., no greater than 500 ppm, e.g., no greater than 250 ppm, e.g., no greater than 200 ppm, e.g., no greater than 100 ppm, e.g., no greater than 50 ppm, e.g., no greater than 25 ppm, e.g., no greater than 10 ppm, e.g., no greater than 5 ppm, e.g., no greater than 2 ppm, e.g., no greater than 1 ppm) and/or ultra-trace level (e.g., less than 1 ppm, e.g., less than 500 ppb, e.g., less than 250 ppb, e.g., less than 100 ppb, e.g., less than 50 ppb, e.g., less than 25 ppb, e.g., less than 10 ppb, e.g., less than 5 ppb, e.g., less than 2 ppb, e.g., less than 1 ppb) of the first gas (e.g., hydrogen sulfide or $H_2O$) in the natural gas sample from the signal corresponding to the received light.

In certain embodiments, the first gas is hydrogen sulfide and wherein the set of one or more discrete or continuous wavelength bands comprises one or both of bands (i) and (ii) as follows: (i) a first band at least 0.05 cm$^{-1}$ in width (e.g., at least 1 cm$^{-1}$, at least 2 cm$^{-1}$, at least 3 cm$^{-1}$, at least 4 cm$^{-1}$, at least 5 cm$^{-1}$, at least 8 cm$^{-1}$) (e.g., and/or no greater than 50 cm$^{-1}$ in width, e.g., no greater than 40 cm$^{-1}$, no greater than 30 cm$^{-1}$, no greater than 20 cm$^{-1}$, no greater than 15 cm$^{-1}$ in width) said first band containing at least one value between 5066 cm$^{-1}$ and 5076 cm$^{-1}$ (e.g., said band containing or overlapping at least partially with 5070±6 cm$^{-1}$); and (ii) a second band at least 0.05 cm$^{-1}$ in width (e.g., at least 1 cm$^{-1}$, at least 2 cm$^{-1}$, at least 3 cm$^{-1}$, at least 4 cm$^{-1}$, at least 5 cm$^{-1}$, at least 8 cm$^{-1}$) (e.g., and/or no greater than 50 cm$^{-1}$ in width, e.g., no greater than 40 cm$^{-1}$, no greater than 30 cm$^{-1}$, no greater than 20 cm$^{-1}$, no greater than 15 cm$^{-1}$ in width) said second band containing at least one value between 5086 cm$^{-1}$ and 5097 cm$^{-1}$ (e.g., said band containing or overlapping at least partially with 5092±6 cm$^{-1}$).

In certain embodiments, the instructions, when executed by the processor, cause the processor to synchronize wavelength scanning of the laser with the detector signal to align, in a time domain, measurement of the detector signal with the wavelength scanning to generate an absorption spectrum.

In certain embodiments, the instructions, when executed by the processor, cause the processor to analyze the generated absorption spectrum [e.g., to perform a chemometric analysis of the generated absorption spectrum either in the time domain or frequency domain (by demodulation), e.g., thereby analyzing spectral absorbance within the one or more discrete or continuous wavelength bands and interference peaks] to determine the trace level and/or ultra-trace level of the first gas (e.g., hydrogen sulfide or $H_2O$) in the natural gas sample.

In certain embodiments, the natural gas sample is at least 20% methane (e.g., at least 30%, at least 40%, at least 50%, at least 60%, at least 70%, at least 80%, or at least 90%) [e.g., wherein methane has an absorption peak that interferes with the absorption peak of the first gas (e.g., hydrogen sulfide or $H_2O$), which is present in the gas sample in only a trace amount (e.g., no greater than 1000 ppm, e.g., no greater than 500 ppm, e.g., no greater than 250 ppm, e.g., no greater than 200 ppm, e.g., no greater than 100 ppm, e.g., no greater than 50 ppm, e.g., no greater than 25 ppm, e.g., no greater than 10 ppm, e.g., no greater than 5 ppm, e.g., no greater than 2 ppm, e.g., no greater than 1 ppm) and/or an ultra-trace amount (e.g., less than 1 ppm, e.g., less than 500 ppb, e.g., less than 250 ppb, e.g., less than 100 ppb, e.g., less than 50 ppb, e.g., less than 25 ppb, e.g., less than 10 ppb, e.g., less than 5 ppb, e.g., less than 2 ppb, e.g., less than 1 ppb)].

In certain embodiments, the instructions, when executed by the processor, identify an absorption peak corresponding to methane in the natural gas sample and use the absorption peak corresponding to methane to line-lock (or, equivalently, to frequency load lock) output wavelength (or frequency) of the laser and stabilize one or more output wavelength bands of the laser (e.g., the set of one or more discrete or continuous wavelength bands), thereby reducing error caused by laser drift without use of a separate reference gas (e.g., methane) cell.

In certain embodiments, the system further comprises a supplemental optical detector for receiving light from the output beam of the laser (e.g., directed by transfer optics from the laser to the supplemental optical detector) that does not pass through the natural gas sample, and for producing a resulting supplemental signal, wherein the instructions, when executed by the processor, analyze the supplemental signal to determine a reference channel baseline signature (e.g., from reproducible modal fluctuations in laser intensity) and subtract the reference channel baseline signature from a sample gas baseline signal (said sample gas baseline signal determined from the photodetector signal corresponding to the light received from the natural gas sample), thereby reducing noise (e.g., determined from the supplemental signal).

In certain embodiments, the system further comprises a sample gas conditioning system (e.g., a heater and/or a temperature controller and/or a filter for conditioning the natural gas sample (e.g., prior to flow of the natural gas sample through the flow cell)).

In certain embodiments, the system further comprises a flow control device for controlling a flow rate of the natural gas sample into/through the flow cell.

In certain embodiments, the system further comprises a pump for controlling and/or reducing pressure of the natural gas sample prior to flow of the sample into/through the flow cell.

In certain embodiments, the system further comprises a vacuum pump (e.g., downstream of the flow cell) for producing a vacuum (reduced pressure) of the natural gas sample in the flow cell (e.g., for measurement of hydrogen sulfide in the natural gas sample) (e.g., wherein the natural gas sample is at least 20% methane—e.g., at least 30%, at least 40%, at least 50%, at least 60%, at least 70%, at least 80%, or at least 90% methane).

In another aspect, the invention is directed to a spectroscopy method [e.g., a tunable diode laser absorption spectroscopy (TDLAS method) or quantum cascade laser (QCL) method] for measuring a trace level and/or an ultra-trace level of a first gas in a natural gas sample, the method comprising: producing an output beam over a set of one or more discrete or continuous wavelength bands at a scan rate from about 0.1 Hz to about 1000 Hz over the set of one or more discrete or continuous wavelength bands [e.g., at a resolution of from 0.01 to 0.0001 $cm^{-1}$, e.g., at an ultra-high resolution, e.g., at a resolution of 0.001 $cm^{-1}$ or lower (/better)] [e.g., by a laser [e.g., a tunable diode laser, such as a distributed feedback laser (DFB), a vertical-cavity surface-emitting laser (VCSEL), an external cavity diode laser or a vertical external-cavity surface-emitting laser (VECSEL)] [e.g., a tunable quantum cascade laser (QCL)]); introducing a natural gas sample into a flow cell, wherein the natural gas sample comprises a trace level (e.g., no greater than 1000 ppm, e.g., no greater than 500 ppm, e.g., no greater than 250 ppm, e.g., no greater than 200 ppm, e.g., no greater than 100 ppm, e.g., no greater than 50 ppm, e.g., no greater than 25 ppm, e.g., no greater than 10 ppm, e.g., no greater than 5 ppm, e.g., no greater than 2 ppm, e.g., no greater than 1 ppm) and/or an ultra-trace level (e.g., less than 1 ppm, e.g., less than 500 ppb, e.g., less than 250 ppb, e.g., less than 100 ppb, e.g., less than 50 ppb, e.g., less than 25 ppb, e.g., less than 10 ppb, e.g., less than 5 ppb, e.g., less than 2 ppb, e.g., less than 1 ppb) of a first gas (e.g., hydrogen sulfide or $H_2O$) (e.g., wherein the natural gas sample is at least 20% methane, e.g., at least 30%, at least 40%, at least 50%, at least 60%, at least 70%, at least 80%, or at least 90% methane); guiding and/or shaping the output beam (e.g., by transmitting optics) from the tunable diode laser to the natural gas sample [e.g., guiding and/or shaping the beam to the flow cell (e.g., a multi-pass cell) through which the natural gas sample flows, e.g., wherein the natural gas sample is an absorbing medium]; receiving light, by an optical detector (e.g., a photodiode or other fast response detector), from the natural gas sample and producing a detector signal corresponding to the received light (e.g., said received light having been transmitted through and/or reflected from transfer optics located between the natural gas sample and the optical detector); and determining, by a processor of a computing device and a memory (non-transitory computer-readable medium) having instructions stored thereon, the trace level and/or ultra-trace level of the first gas in the natural gas sample from the signal corresponding to the received light.

In certain embodiments, the first gas is hydrogen sulfide and wherein the set of one or more discrete or continuous wavelength bands comprises one or both of bands (i) and (ii) as follows: (i) a first band at least 0.05 $cm^{-1}$ in width (e.g., at least 1 $cm^{-1}$, at least 2 $cm^{-1}$, at least 3 $cm^{-1}$, at least 4 $cm^{-1}$, at least 5 $cm^{-1}$, at least 8 $cm^{-1}$) (e.g., and/or no greater than 50 $cm^{-1}$ in width, e.g., no greater than 40 $cm^{-1}$, no greater than 30 $cm^{-1}$, no greater than 20 $cm^{-1}$, no greater than 15 $cm^{-1}$ in width) said first band containing at least one value between 5066 $cm^{-1}$ and 5076 $cm^{-1}$ (e.g., said band containing or overlapping at least partially with 5070±6 $cm^{-1}$); and (ii) a second band at least 0.05 $cm^{-1}$ in width (e.g., at least 1 $cm^{-1}$, at least 2 $cm^{-1}$, at least 3 $cm^{-1}$, at least 4 $cm^{-1}$, at least 5 $cm^{-1}$, at least 8 $cm^{-1}$) (e.g., and/or no greater than 50 $cm^{-1}$ in width, e.g., no greater than 40 $cm^{-1}$, no greater than 30 $cm^{-1}$, no greater than 20 $cm^{-1}$, no greater than 15 $cm^{-1}$ in width) said second band containing at least one value between 5086 $cm^{-1}$ and 5097 $cm^{-1}$ (e.g., said band containing or overlapping at least partially with 5092±6 $cm^{-1}$).

In certain embodiments, the method further comprises synchronizing, by the processor, wavelength scanning of the laser with the detector signal to align, in a time domain, measurement of the detector signal with the wavelength scanning to generate an absorption spectrum.

In certain embodiments, the method further comprises analyzing, by the processor, the generated absorption spectrum [e.g., performing a chemometric analysis of the generated absorption spectrum either in the time domain or frequency domain (by demodulation), e.g., thereby analyzing spectral absorbance within the one or more discrete or continuous wavelength bands and interference peaks] to determine the trace level and/or ultra-trace level of the first gas (e.g., hydrogen sulfide or $H_2O$) in the natural gas sample.

In certain embodiments, the natural gas sample is at least 20% methane (e.g., at least 30%, at least 40%, at least 50%, at least 60%, at least 70%, at least 80%, or at least 90%) [e.g., wherein methane has an absorption peak that interferes with the absorption peak of the first gas (e.g., hydrogen sulfide or $H_2O$), which is present in the gas sample in only a trace amount (e.g., no greater than 1000 ppm, e.g., no greater than 500 ppm, e.g., no greater than 250 ppm, e.g., no greater than 200 ppm, e.g., no greater than 100 ppm, e.g., no greater than 50 ppm, e.g., no greater than 25 ppm, e.g., no greater than 10 ppm, e.g., no greater than 5 ppm, e.g., no greater than 2 ppm, e.g., no greater than 1 ppm) and/or an ultra-trace amount (e.g., less than 1 ppm, e.g., less than 500 ppb, e.g., less than 250 ppb, e.g., less than 100 ppb, e.g., less than 50 ppb, e.g., less than 25 ppb, e.g., less than 10 ppb, e.g., less than 5 ppb, e.g., less than 2 ppb, e.g., less than 1 ppb)].

In certain embodiments, the method further comprises identifying, by the processor, an absorption peak corresponding to methane in the natural gas sample; and using the absorption peak corresponding to methane to line-lock (or, equivalently, to frequency load lock), by the processor, output wavelength (or frequency) of the laser and stabilize one or more output wavelength bands of the laser (e.g., the set of one or more discrete or continuous wavelength bands), thereby reducing error caused by laser drift without use of a separate reference gas (e.g., methane) cell.

In certain embodiments, the method further comprises receiving light (e.g., by a supplemental optical detector) from the output beam of the laser (e.g., directed by transfer optics from the laser to the supplemental optical detector) that does not pass through the natural gas sample; producing a resulting supplemental signal; and analyzing, by the processor, the supplemental signal to determine a reference channel baseline signature and subtracting the reference channel baseline signature from a sample gas baseline signal (said sample gas baseline signal determined from the photodetector signal corresponding to the light received from the natural gas sample), thereby reducing noise.

In certain embodiments, the method further comprises conditioning the natural gas sample (e.g., using a heater, and/or a temperature controller, and/or a filter) (e.g., prior to flow of the natural gas sample through the flow cell).

In certain embodiments, the method further comprises controlling a flow rate of the natural gas sample into/through the flow cell (e.g., via a flow control device).

In certain embodiments, the method further comprises controlling and/or reducing pressure of the natural gas sample prior to flow of the sample into/through the flow cell (e.g., via a pump).

In certain embodiments, the method further comprises producing a vacuum (reduced pressure) (e.g., by a vacuum pump) of the natural gas sample in the flow cell (e.g., for measurement of hydrogen sulfide in the natural gas sample) (e.g., wherein the natural gas sample is at least 20% methane—e.g., at least 30%, at least 40%, at least 50%, at least 60%, at least 70%, at least 80%, or at least 90% methane).

In another aspect, the invention is directed to a system for measuring hydrogen sulfide in natural gas, comprising: a light source emitting light at a frequency substantially corresponding to an absorption line of hydrogen sulfide in the 5066-5076 $cm^{-1}$ (1970-1974 nm) wavelength range and/or 5086-5097 $cm^{-1}$ (1962-1966 nm) wavelength range, wherein the light source is positioned to emit light through the natural gas; a first detector configured to detect an intensity of the light emitted from the light source; a second detector configure to detect an intensity of the light after passing through the natural gas; and a processing module coupled to the first and second detector for determining the level of hydrogen sulfide in the natural gas.

In certain embodiments, the light source scans over the wavelength range at a rate from 10 Hz to 200 Hz.

In certain embodiments, the signals from the detectors are sampled with a resolution from 0.01 to 0.0001 $cm^{-1}$.

Elements of embodiments involving one aspect of the invention (e.g., methods) can be applied in embodiments involving other aspects of the invention (e.g., systems), and vice versa.

BRIEF DESCRIPTION OF THE DRAWINGS

The advantages described herein, together with further advantages, may be better understood by referring to the following description taken in conjunction with the accompanying drawings. The drawings are not necessarily to scale, emphasis instead generally being placed upon illustrating the principles of the embodiments.

DETAILED DESCRIPTION

Figure 1:
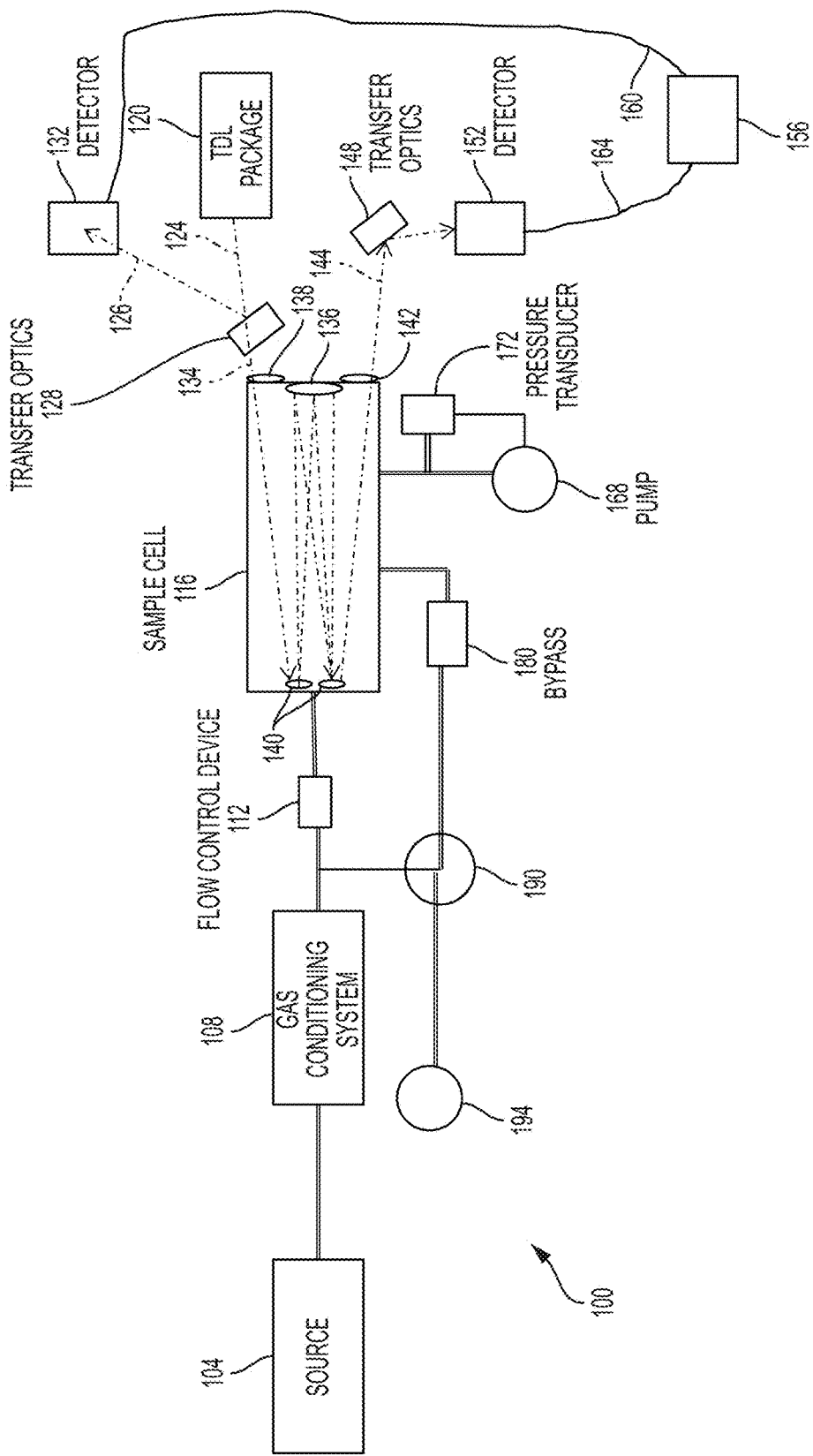
FIG. 1 is a schematic illustration of a system for measuring hydrogen sulfide in natural gas, according to an illustrative embodiment.

Embodiments described herein relate to absorption spectroscopy systems and methods for measurement of hydrogen sulfide in natural gas. The systems and methods are based on absorption of electromagnetic (EM) energy at specific wavelengths where hydrogen sulfide strongly absorbs the energy. Embodiments described herein are also related to measurement of water and other substance and compounds in natural gas.

Hydrogen sulfide has absorbance features in both the Mid-IR (MIR) and Near-IR (NIR) EM regions. MIR regions are typically stronger than the NIR absorbance bands. However, the overlap of many other compound absorbance bands, such as water, with $H_2S$ bands in the MIR regions is problematic for many instruments to accurately detect the compounds. The MIR regions also, typically, require the use of Quantum Cascade Lasers (QCL) to generate the frequencies in these areas of the EM spectrum. The use of weaker NIR absorbance bands result in lower signal to noise ratio and there are also interferences from, most notably, methane ($CH_4$), carbon dioxide ($CO_2$) and alkanes (e.g., propane ($C_3H_8$)).

A TDL is a type of laser, which stands for "Light Amplification by Stimulated Emission of Radiation." It is a laser diode, similar to a light emitting diode (LED), which has a junction between two semiconductors (one positive, one negative). This junction is known as a p-n junction. These semiconductors are incredibly small, made of very thin slices of semiconducting material, and are very carefully manufactured so as to create the p-n junction. A TDL is a laser that, because of its semiconductor construction and elemental make-up, allows the laser to lase in a narrow region of interest. Then, a very narrow emission line can be selected by using an internal or external Bragg grating (or similar device) or external etalon to scan across absorbance features of a target compound.

For example, when using an internal Bragg grating, the laser diode's frequency tuning is accomplished by changing the temperature of the internal or external grating which changes the spacing of the grating and the frequency of the EM oscillation mode in the device to change the frequency that is being emitted by the semiconductor device. The temperature may be changed by directly controlling the grating temperature with a device such as a Peltier Thermoelectric cooler (TEC), or by changing the pumping current provided to the TDL so that more excess waste heat is generated which influences the temperature of the grating. The output frequency of the TDL may also be tuned using an external etalon that may also be temperature influenced to achieve the reproducible frequencies of interest. Frequency chirping is another way of tuning wavelength, which involves turning the laser on and off so the laser heats up and cools down quickly and sweeps over a series of frequencies of interest. However, the proper center frequency of interest must be specified during the TDL device fabrication process so that it is close to the frequencies of interest. This is typically required because TDL's are able to operate in relatively narrow bands around the center frequency of the device. In addition, TDL technology was previously developed for transmission of digital data through fiber optic cable. The operating characteristics of available TDL's have not focused on areas of the electromagnetic spectrum where overlapping frequencies exist (e.g., for example, in gas analysis, where many compounds have spectral features that overlap with each other).

Lasers are monochromatic. For a laser to function, within the cavity, many photons of light of the same frequency will travel coaxially due to the constraints of the waveguide, causing them to constructively interfere with each other, which stabilizes the electromagnetic wave's oscillation and propagation modes. In a laser diode, the light is emitted because there are both electrons, in the negative substance, and holes (the absence of electrons) in the positive substance. When the negative substance is charged, the electrons in the negative substance jump to fill the holes in the positive substance. When the electrons jump, they lose energy in the form of photons, which are "light quanta," or small indivisible packets of light. Because all the electrons jumped down to fill holes in a certain semiconducting material, all of the photons are of the same frequency. This causes a laser beam to form and come out the facet of the laser diode. Some of the beam reflecting back through the cavity helps stimulate this process and thus amplify the light emission process.

In certain embodiments, the laser is operated in a constant current mode. In this mode, no feedback diode is required. However, in certain embodiments that operate in a constant power mode, a feedback diode is required. Because laser diodes have to be operated at a relatively high current density, and have a low forward resistance when lasing action occurs, they are at risk of destroying themselves due to thermal runaway. Their operating light density can also rise to a level where the coating of the waveguide can start delaminating. This means that a laser diode's current must be regulated by a constant current circuit (rather than a simple series resistor), and a laser device needs to be temperature controlled by a TEC. Running in the constant power mode, most laser diodes have a silicon PIN photo-diode built right into the package, arranged so that it automatically receives a fixed proportion of the laser's output to monitor the laser's output. The output of this monitor diode can then be used to either limit or control the current fed through the laser by the current control circuit, for stable and reliable operation.

FIG. 1 is a schematic illustration of a system 100 for measuring hydrogen sulfide in natural gas, according to an illustrative embodiment. A source 104 of gas (e.g., a natural gas pipeline) supplies the sample gas to a gas conditioning system 108. The gas conditioning system 108 is configured to; for example, optionally reduce the pressure of the gas from the supply pressure level of, for example, a natural gas pipeline, for further processing. In some embodiments, the gas conditioning system 108 also heats the gas and/or reduces particulates in the gas by filtering the gas. The heating addition is to prevent phase changes to the sample gas and prevent any moisture or hydrocarbon condensation due to the Joule-Thompson effect of a rapidly de-pressurizing gas. Adding heat to the system prevents this phenomenon from occurring and allows for an accurate reading of the gas sample composition on a volume to volume concentration basis. Heating the sample aids in maintaining consistent properties in the sample, so the spectral lines stay uniform. In addition, heating the sample to, for example, 50-60° C. prevents the sample from condensing on the optics by keeping the sample in a vapor phase.

The conditioned gas is then delivered to a flow control device 112 which controls the flow rate of the gas into a sample cell 116. The flow control device 112 can be, for example, an orifice or valve used to vary the flow of gas. A light source 120 (e.g., a TDL package) outputs a light beam 124 at a desired frequency to a set of transfer optics 128. The transfer optics 128 include one or more mirrors, lenses, and/or filters to modify the shape or orientation of the light beam 124 as necessary to direct it to subsequent optical components in the system 100. To measure hydrogen sulfide in the gas, the TDL package 120 outputs the light 124 at a frequency substantially corresponding to an absorption line of hydrogen sulfide in the 5066-5076 $cm^{-1}$ (1970 to 1974 nm) or the 5086-5097 $cm^{-1}$ (1962-1966 nm) wavelength range. Selection of absorbance peaks from the hundreds of other frequencies where other target compounds are present in percent or trace level concentrations exist is not a trivial task. By analytically and experimentally identifying this particular wavelength band, Applicant is able to detect $H_2S$ with sensitivity and accuracy levels in natural gas that is necessary for practical use.

A complex method was used to choose the peaks of interest that would be successful in measuring trace levels of $H_2S$ in a high concentration hydrocarbon background as found in typical natural gas sample matrices. The technical challenge of the measurement was to separate trace $H_2S$ (sub-ppm level) from very rich $CH_4$ background (e.g., as found in typical natural gas sample matrices, e.g., a pipeline gas) (e.g., from about 90% to about 100%, e.g., near 100% level) and other lower percentages of hydrocarbons, and ppm levels of carbon dioxide, sulfurs, and moisture. Traditional optical measurement with an incoherent light source cannot detect such a wide dynamic range with a resolution typically no better than 0.1 $cm^{-1}$, thus making it difficult to separate a heavily overlapped absorption spectrum between $H_2S$ and $CH_4$. Therefore, a distributed feedback (DFB) laser was used as the source, which can reach a much better resolution; typically better than 0.001 $cm^{-1}$. At this resolution, the individual absorption peaks can be resolved and $H_2S$ peaks can be separated from $CH_4$ absorption peaks for quantification. In this work, it was demonstrated that with DFB tunable laser absorption spectroscopy (DFB-TDLAS), a sub-ppm level $H_2S$ detection in a natural gas background can be achieved.

Selectivity of $H_2S$ with the existence of 90-100% $CH_4$ was a major hurdle. The absorption line of $H_2S$ had to be adjacent to relatively weak $CH_4$ absorption bands; otherwise, the interference will exceed the capability of any data processing method. Modeling work was based on a HITRAN database.

Figure 3:
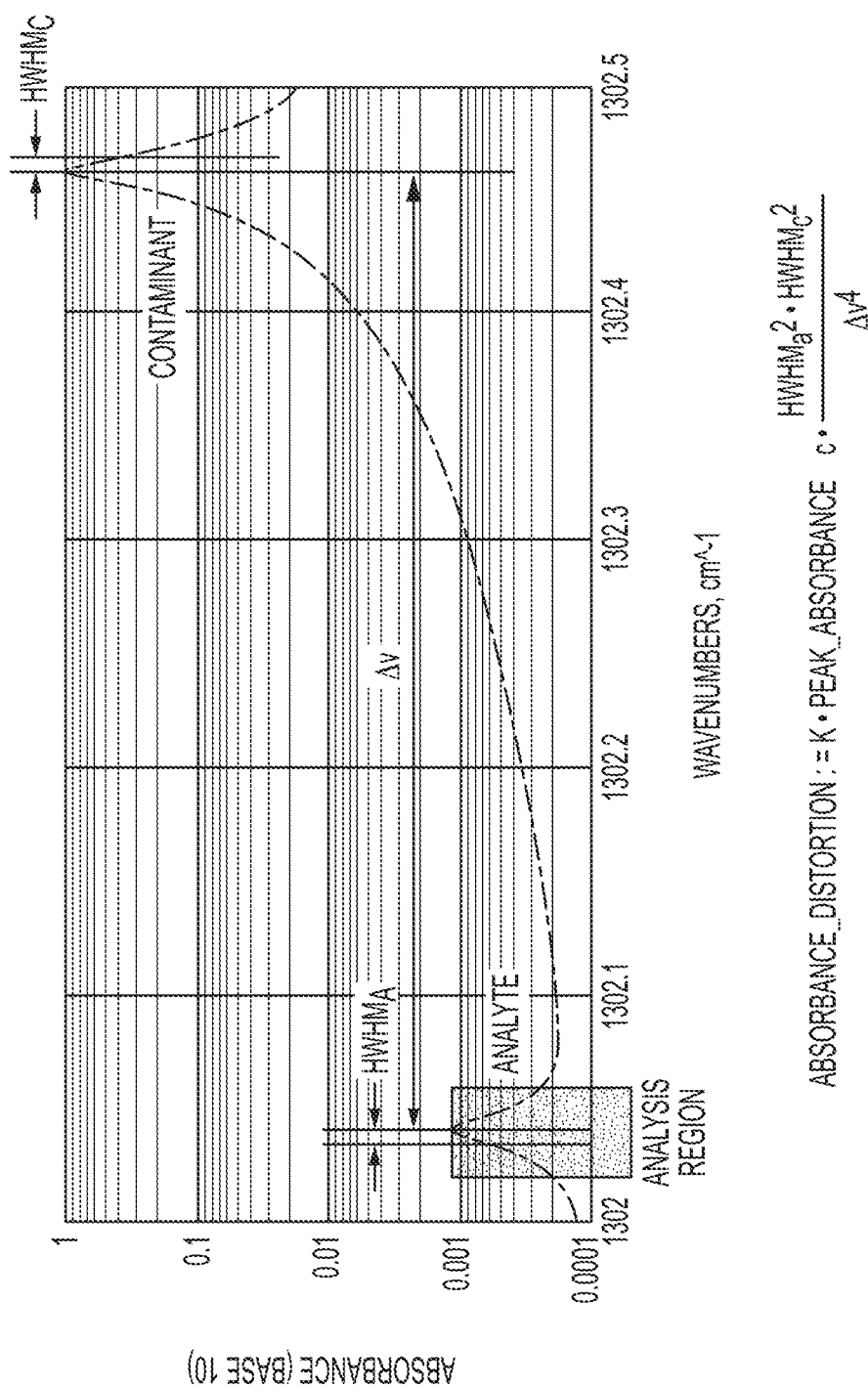
FIG. 3 is a plot of laser absorption lines illustrating how the proximity of one line relative to another affects the shape of each peak, according to an illustrative embodiment.

FIG. 3 is a plot of laser absorption lines illustrating that the proximity (distance) of one line relative to another line will affect the shape of each peak by the equation provided in the figure. To properly perform a simulation model on the effects that nearby peaks had on the target peak ILS, the equation for the distortion that nearby Lorentzian lines had on the target peak for $H_2S$ is simulated (e.g., at low pressures, e.g., at pressures of about 100 Torr or less) and applied to all possible target compound absorption peaks in the target compound spectrum. The target compound spectrum for $H_2S$ contains hundreds of possible peaks for quantification. To properly choose a peak as a target for quantification, the peaks had to be examined and the distortion quantified as to the effect of all possible other compounds in the sample matrix that might be present. The distortion was measured and quantified by holding the target compound peak concentration constant and perturbing any nearby peak compounds concentration for each of the possible interferents that may be present in the sample matrix. This method of calculating interferences is a worst case analysis, and does not account for improvements that may occur from using multi-component chemometrics models. Additionally, sensitivity based on that peaks absorptivity coefficient was also examined. Both of these factors were simulated to choose the best target compound peak to use for quantification. Laser sources were then investigated to choose one that had the proper emission range and to determine if it existed or needed to be developed. It was discovered that laser sources at these frequencies did not exist and needed to be developed at the request of the Applicant. Interferences from hydrocarbons other than $CH_4$ were also studied. Coupling with the full scan from a Fourier Transform Infrared Spectrometer (FTIR), the interference influence of other gases commonly found in the sample matrix on the selected wavelength was derived.

Figure 4:
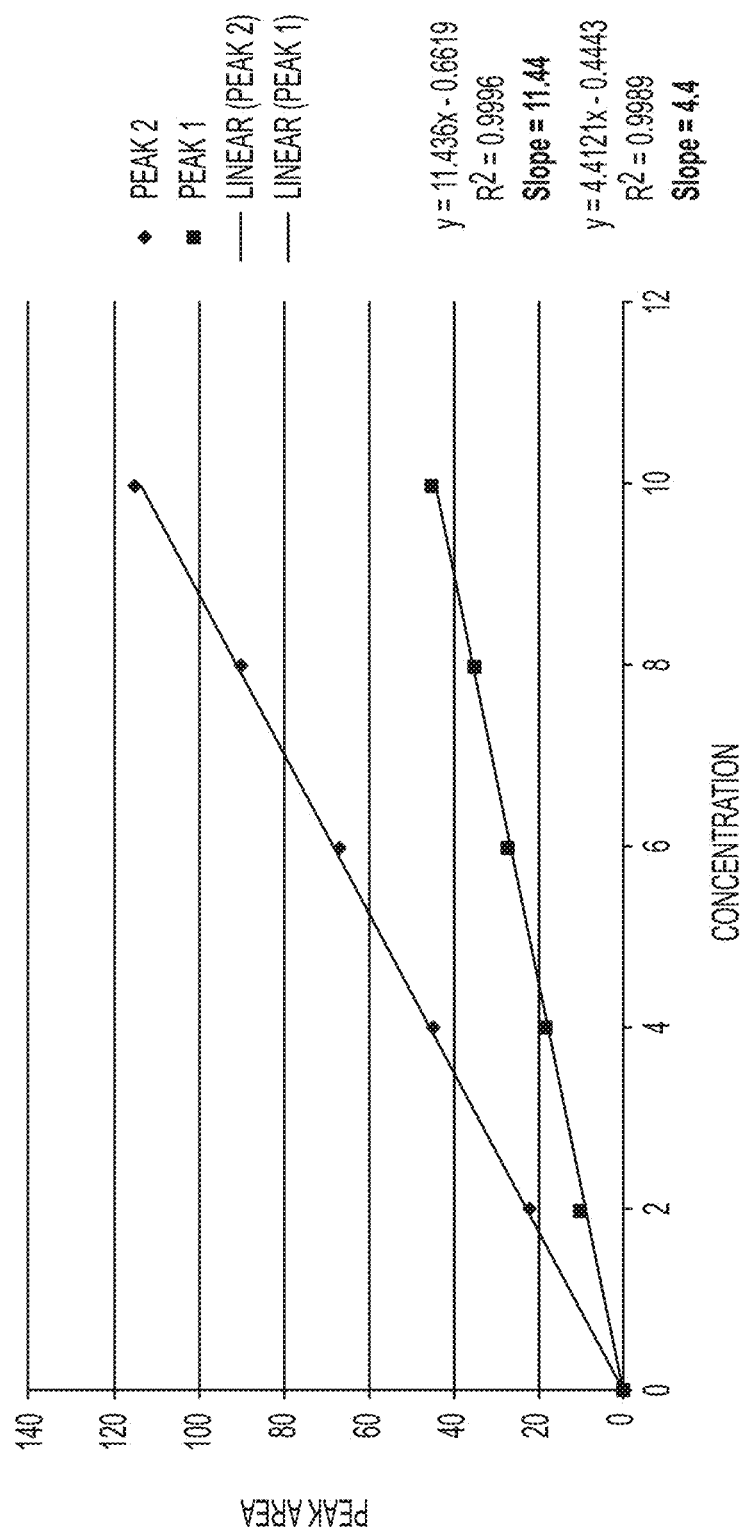
FIG. 4 is a plot illustrating absorptivity coefficient examples for different peaks selected for quantification, according to an illustrative embodiment.
Figure 5:
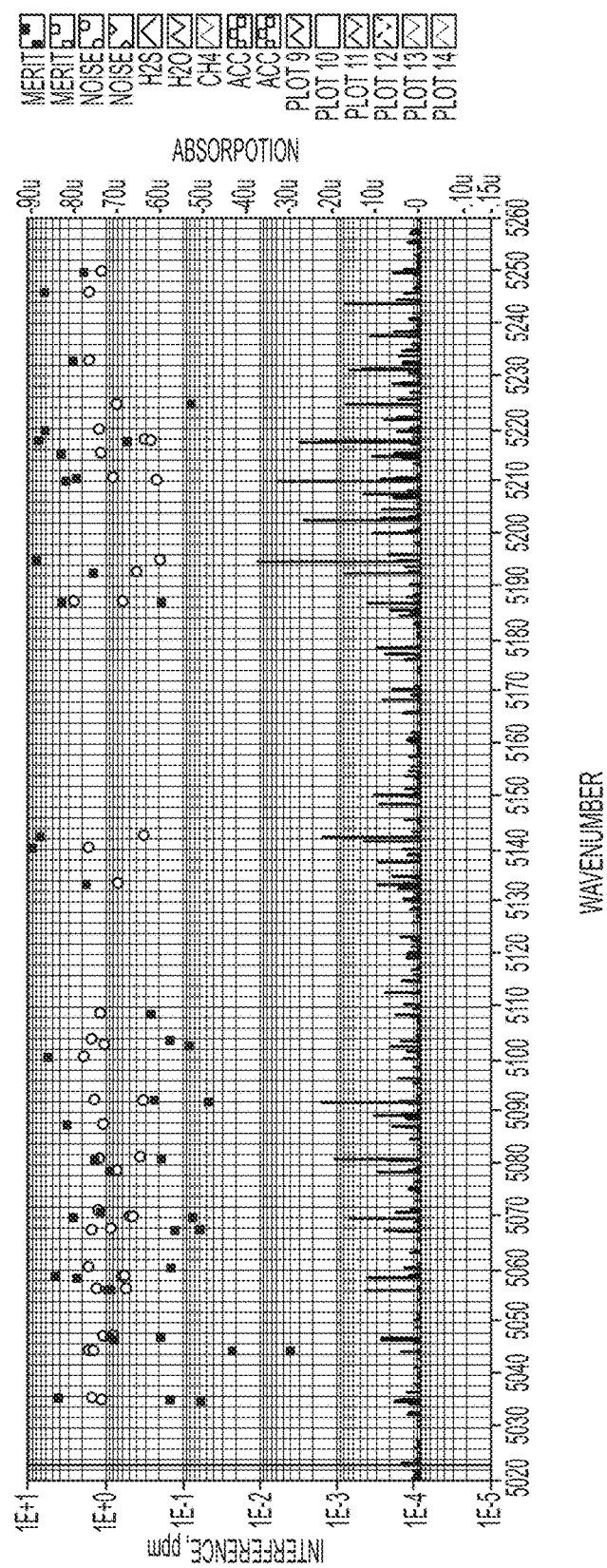
FIG. 5 is a plot of a merit and sensitivity score chart for different $H_2S$ absorption lines, according to an illustrative embodiment.

To achieve better separation between adjacent absorption lines, the gas sensor was run at 0.1 atm pressure to narrow the absorbance bands without substantially changing the peak height of the bands. There were two major constraints on selecting the right wavelength for $H_2S$ measurement: (1) strength of the absorption of $H_2S$; (2) strength of the adjacent $CH_4$ absorption line and (3) spacing between the two lines. In FIG. 5, the visual representation from the merit scores show the distortion effects from nearby peaks and the sensitivity of the peaks based on the absorptivity coefficient for that peak (slope of the function for peak area vs. concentration from the calibration curve for that peak) for each individual peak in relation to the noise level of the baseline at that peak frequency of the target compound $H_2S$ as represented in FIG. 4. FIG. 4 illustrates absorptivity coefficient examples for different peaks selected for quantification (this is the sensitivity data and correspond to the circles in FIG. 5). A larger slope value indicates a more sensitive peak.

FIG. 5 shows the comparison between different $H_2S$ absorption lines. The circles above the peaks are noise levels at each line, which is inversely proportional to the absorption strength of the line and proportional to the noise from the source and electronics given a specific observation time. The squares above the peaks are merit scores of the line, which evaluate the influence (distortion) of the interference from the adjacent absorption lines from other gases found in the sample matrix. In FIG. 5, a lower score for each symbol is more desirable—the desire is to have low squares and circles. The following gases, $CH_4$, $H_2O$ and $CO_2$ were considered for distortion calculations. In this graph, there are two candidate lines having both the low noise and low interference for successful $H_2S$ detection and quantification: 5070 $cm^{-1}$ and 5092 $cm^{-1}$. These two lines are the selected bands for this illustrative embodiment. The same scoring system was used to explore the full range in the near to mid IR range. These two lines were the best candidates for selection and development of hardware.

Figure 6:
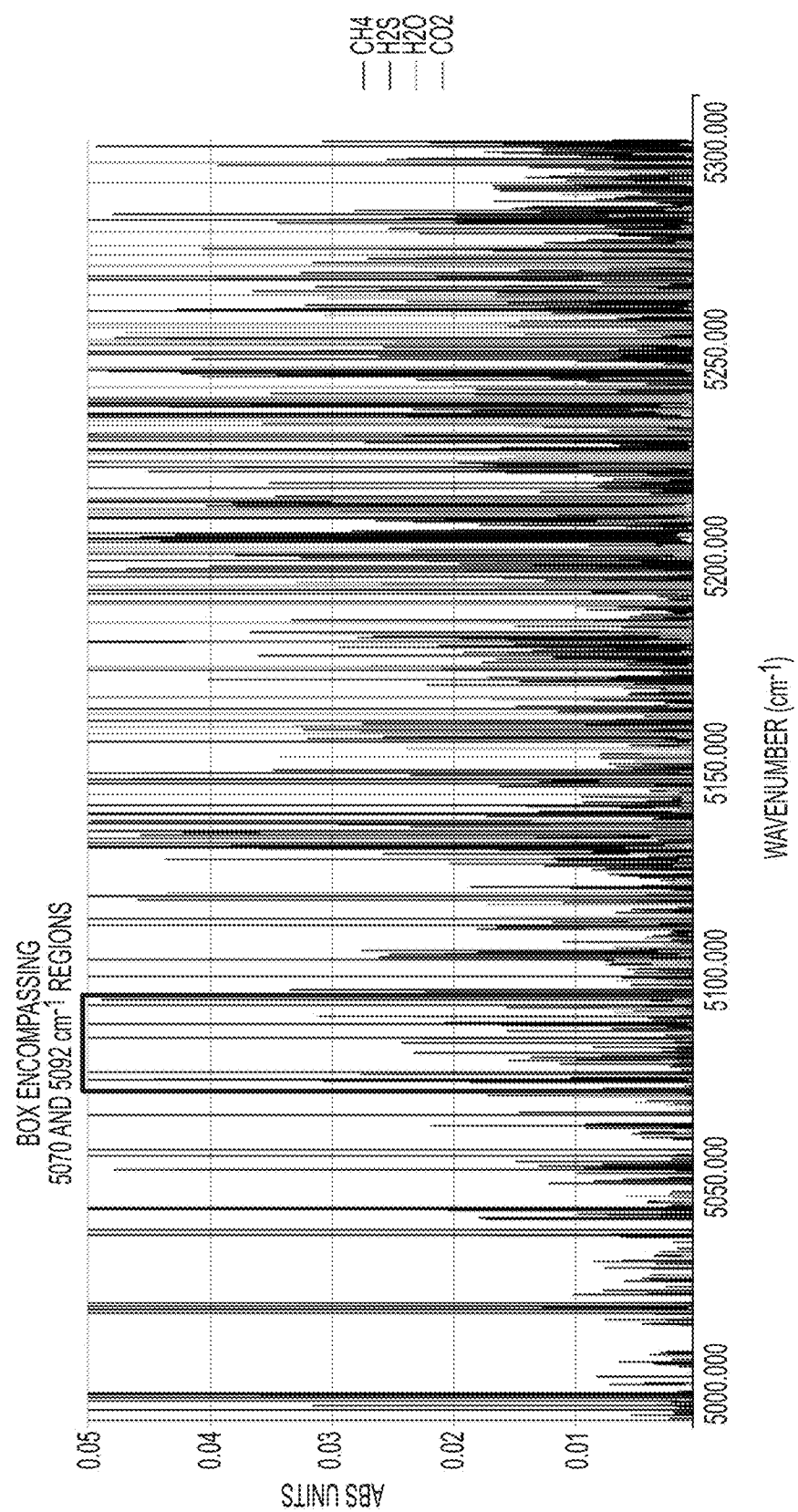
FIG. 6 is a plot of peaks over a range of wavenumbers, including two candidate bands for $H_2S$ detection and quantification demonstrating low noise and low interference, according to an illustrative embodiment.

In FIG. 6, the region that contains the two selected peaks is represented by the box in part of the NIR region considered for this illustrative embodiment. The entire MID and NIR spectral regions comprising 650-7000 $cm^{-1}$ were considered in this study. The boxed area is where low squares and circles are present. Hundreds of peaks represented in just the 300 $cm^{-1}$ window of the NIR region can be seen. Identifying wavelength ranges is very complex because it would not be possible to just pick a region or wave number by visually searching for a candidate peak. The entire MIR and NIR EM spectrum comprising over a thousand candidate peaks was considered. From these simulations, the two best candidate peaks were identified. Hardware was then developed for these target peaks.

Figure 7:
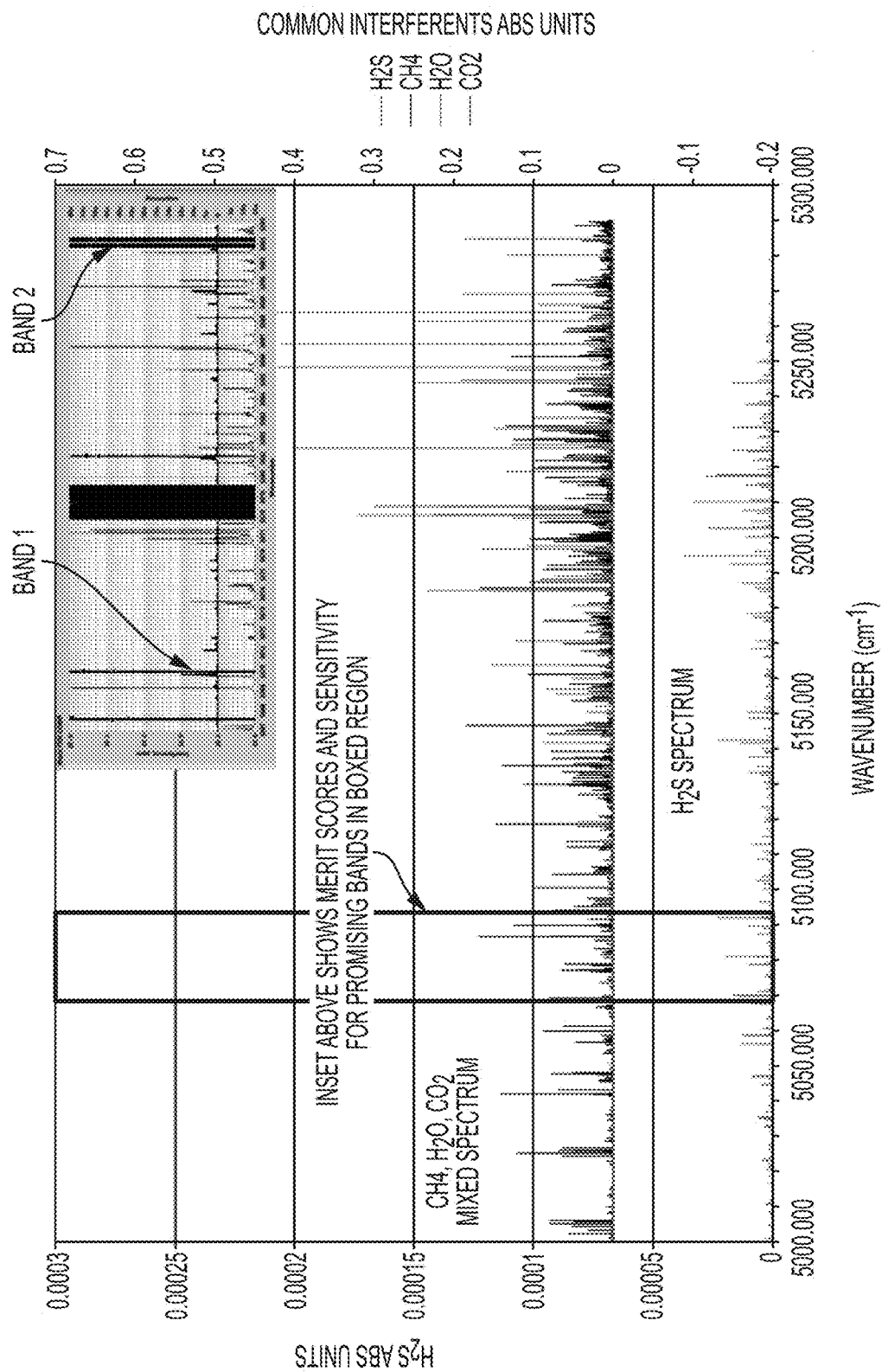
FIG. 7 is a plot with an inset expanding the box containing the two candidate peaks in FIG. 6, according to an illustrative embodiment.

In FIG. 7, the box containing the two candidate peaks was zoomed in further in the inset to demonstrate the box region identified still contained a large number of candidate peaks. When overlaid with the three interferences modeled and identified as a "mixed spectrum", a visual identification of these two candidate peaks would be impossible to identify among the vast number of interfering species absorption bands. FIG. 7 shows a region of candidate peaks identified by the models in relation to a subset of the NIR spectrum showing both target compound peaks (bottom spectrum) and a mixture of interfering peaks in one spectrum (top spectrum). In the inset, the top spectrum is for the target compound and the bottom spectra are interferents.

Figure 8:
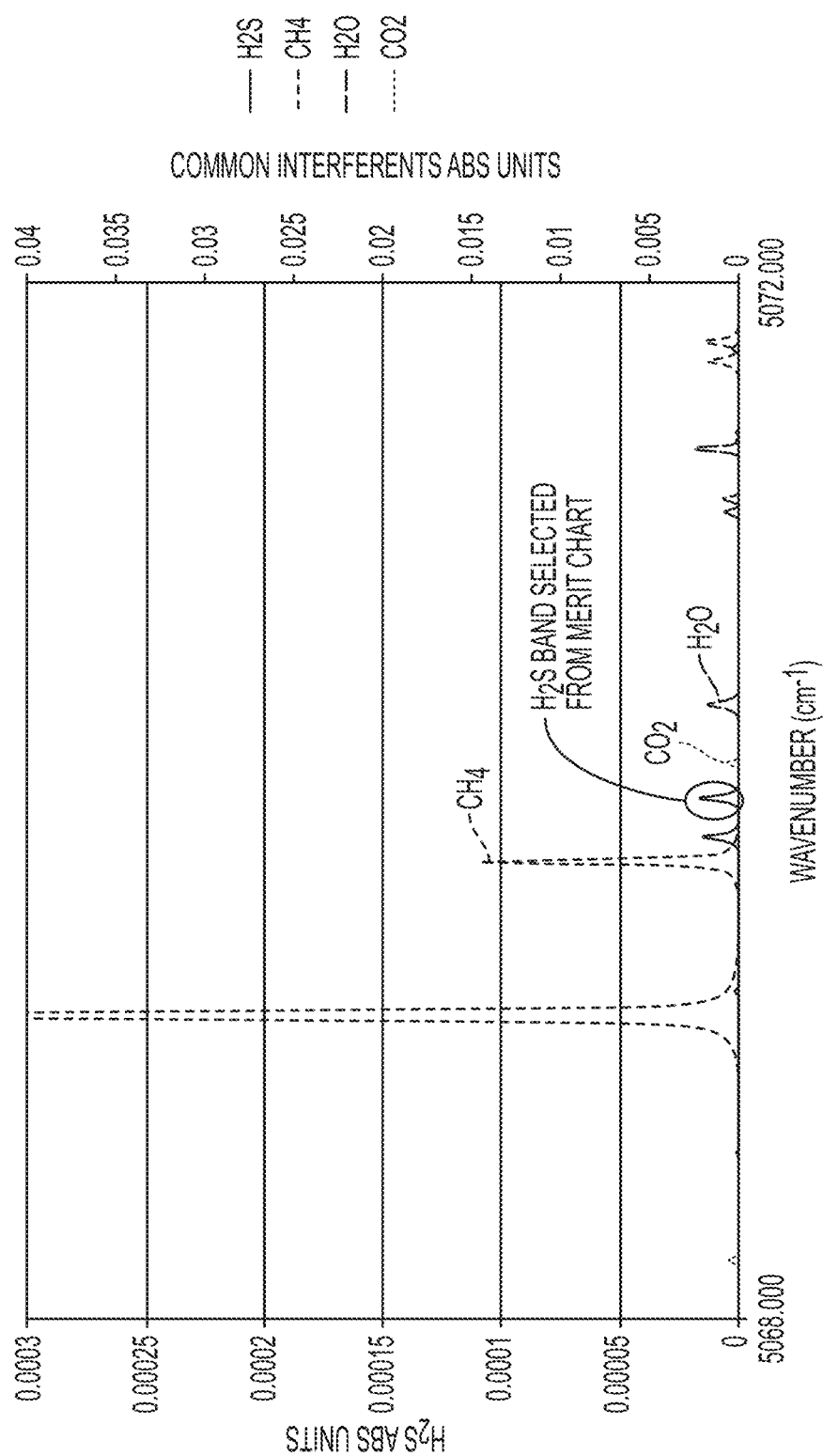
FIG. 8 is a plot illustrating a further zoom-in of the window "Band 1" identified in FIG. 7, according to an illustrative embodiment.

In FIG. 8, further zooming in of the window depicted in FIG. 7, identified as containing the two target peaks of Band 1 for successful $H_2S$ identification and quantification in a hydrocarbon rich sample matrix such as pipeline gas, demonstrates the model was successful in its selection of two peaks out of over a thousand other candidate peaks for development of this illustrative embodiment. Band 1 is the 5066-5076 $cm^{-1}$ (1970 to 1974 nm). Band 2 (also shown in FIG. 7) is the 5086-5097 $cm^{-1}$ (1962-1966) nm wavelength range, which also confirmed that the model was successful. Visual determination of these two bands would have been nearly impossible to perform without the use of this dual factor model and the further simulation verification using surrogate absorption bands from a laser used in this study.

In certain embodiments, the output frequency of the light source 120 is varied so it is repeatedly scanned across the wavelength range at a rate of 1 Hz to 1 KHz, where the output frequency of the light source 120 is varied and ultimately sampled by the electronics with a resolution of between 0.01 and 0.0001 $cm^{-1}$. The ability to scan across an absorbance feature using a narrow band TDL (or QCL) with an ultra-high (0.001 $cm^{-1}$ or better) resolution, allows the user to then be able to obtain information on the spectral absorbance peak of the compound. These features may then be used with their interference peaks in powerful chemometrics models to further improve limits of detection (LOD).

The transfer optics 128 are configured to reflect a portion of the light 126 to detector 132 and another portion of the light 134 to the sample cell 116. The light 126 reflected by the transfer optics 128 is directed to a first detector 132 where it is measured by the detector. The detector 132 is therefore used to detect spectral properties (e.g., intensity, spectral content) of the light that is emitted by the TDL package 120, but which is not passed through a sample gas in the cell 116. The use of two detectors (132 and 152) results in the ability to subtract out the reference channel baseline signature (not subjected to the sample gas matrix) from the sample gas baseline to reduce the noise level of the measurement and improve the LOD of $H_2S$ gas concentration in the sample matrix.

The light 134 that enters the sample cell 116 passes through a lens 138 in the body of the sample cell 116. Generally, the goal of this type of sample cell is to improve detection sensitivity by increasing the total optical path length that light travels through a small sample volume. A longer path length results in greater detection sensitivity. Focusing mirrors are used in the sample cell to redirect the light at each reflection point, resulting in the light beam being restricted to a predefined space along a controlled path until it exits the sample cell. The output of the cell is the input of an optical detector, which detects specific changes in the properties of the light that occur during interaction with the sample in the cell. After the light 134 passes into the sample cell 116, the light 134 is reflected back and forth within the cell 116 between a field mirror 136 and two objective mirrors 140 opposite the field mirror 136. Optical cells in which light is reflected back and forth multiple times are often referred to as multi-pass cells. White cells and Herriott cells are two examples of multi-pass cells used in spectroscopy applications such as this one. In certain embodiments, the cell 116 and mirrors 136 and 140 are configured to reflect the light back and forth multiple times until the light travels a sufficient distance to interact with the sample in the cell 116 to achieve the desired measurement sensitivity. In certain embodiments, the cell 116 and mirrors 136 and 140 are configured so the light travels 10.2 meters before exiting the cell 116 via lens 142.

Light 144 exiting the cell 116 passes to a set of transfer optics 148, which direct the light 144 to a second detector 152. The detector 152 is therefore used to detect spectral properties (e.g., intensity, spectral content) of light that is emitted by the TDL package 120, but which passes through the sample in the cell 116. The detectors 132 and 152 convert the received light into signals 160 and 164, respectively, which correspond to the spectral properties of the light measured by the detectors. For example, the signals 160 and 164 may be voltage signals proportional to the spectral properties of the received light. In certain embodiments, the detectors 132 and 152 are non-liquid nitrogen cooled detectors responsive to the target compound region of interest that is based on a semiconductor technology selected from the group: mercury cadmium telluride (MCT), deuterated triglycine sulfate (DTGS), Indium Arsenide, Indium Antinomide, Indium Gallium Arsenide, or other diode or semiconductor type material.

The detectors 132 and 152 output the signals 160 and 164, respectively, to a processing module 156. The processing module 156 (e.g., a computer processor or analog electronics) synchronizes the wavelength scanning of TDL 120, and the detector signal acquisition, which generates absorption spectra of the sample gas in the sample cell 116. The synchronization allows one to align, in the time domain, the measurement of the detector signal to the driving of the laser so it is possible to assign the correct wavenumbers more accurately to the spectrum generated by the detector. The processing module 156 also conducts the chemometrics analysis on the absorption spectra either in the time domain or frequency domain (by demodulation) to differentiate different components in the gas mixture.

In certain embodiments, the pressure in the sample cell 116 is reduced by a pump 168 to a desired level as measured by a pressure transducer 172. The pump 168 can be, for example, a vacuum pump that is used to lower the pressure in the cell 116. In certain embodiments, the pressure in the sample cell 116 is lowered below ambient air pressure (i.e., below 1 atmosphere at sea level) to improve the sensitivity of the system 100 to detect the substances (e.g., $H_2S$) in the sample cell. In certain embodiments, the pressure is lowered to, for example, as much as 1/20 atmosphere or lower, to slightly less than 1 atmosphere. In some embodiments, the pressure will be maintained at 1 atm. The operational pressure will depend on the presence of interfering species peaks where lower pressure is required to narrow the absorbance peak full width-half height so that the target gas $H_2S$ absorbance or modulated peak is resolved from any other peaks. Reducing the gas pressure reduces the spectral linewidth of all gases in the sample. By reducing the pressure of natural gas in the sample cell, the system 100 reduces the interference of the natural gas and increases the sensitivity and accuracy of the system in measuring $H_2S$ in the sample cell 116. The bypass 180 is used to allow the sample gas, which has been measured for $H_2S$ concentration, to come to ambient pressure so that additional moisture peaks may be measured at 1 atm. A three-way valve 190 is used to release the vacuum in the system or allow the system to come to ambient pressure. Device 194 is an alternative pressure source that can be used to alter the pressure within the system.

Figure 2:
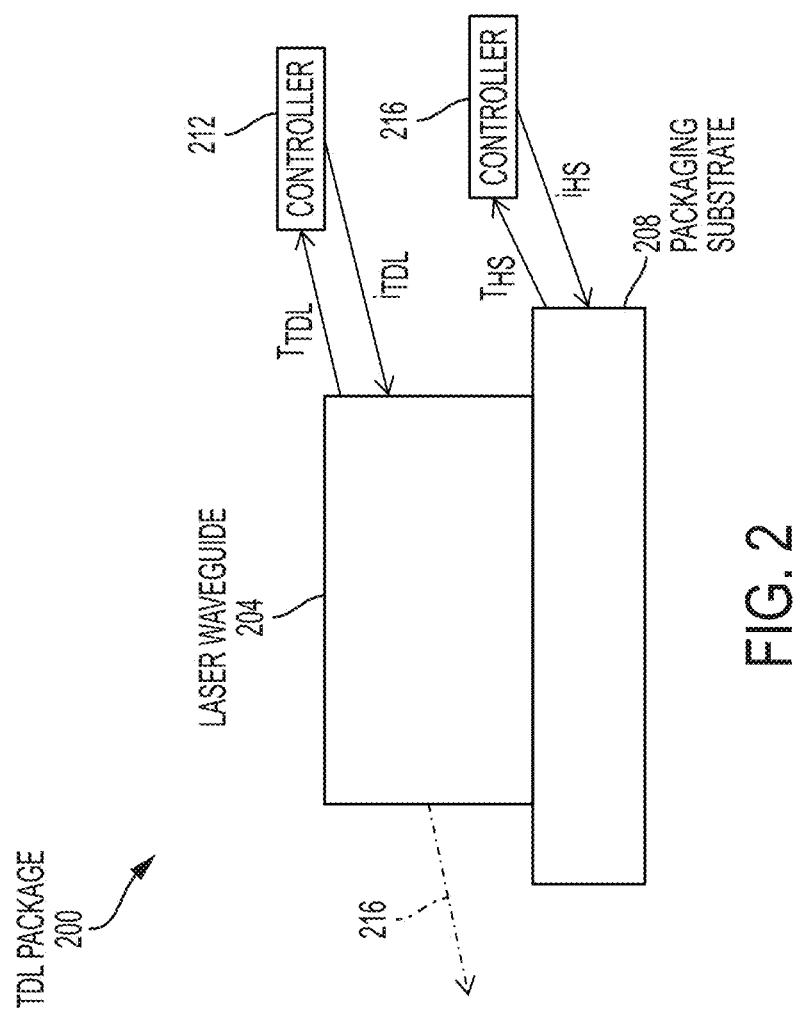
FIG. 2 is a schematic illustration of a Tunable Diode Laser (TDL) package, according to an illustrative embodiment.

FIG. 2 is a schematic illustration of a TDL package 200, according to an illustrative embodiment. The package 200 includes a laser waveguide 204 and a packaging substrate 208. The packaging substrate 208 is operatively coupled to the laser waveguide 204 to control the temperature of the laser waveguide 204. The package 200 also includes a controller 216 that is used to control the temperature of the packaging substrate 208. The controller 216 receives a temperature from the packaging substrate 208 and outputs a current signal to the packaging substrate 208 to control or, for example, maintain the packaging substrate 208 at a desired temperature in order to stabilize the temperature of the laser waveguide 204. Controller 212 is coupled to the laser waveguide 204 to control the current supplied to the laser waveguide 204. The frequency of the light 216 output by the TDL package 200 is controlled by changing the temperature of the laser diode, which is a function of both packaging substrate 208 temperature and current supplied by controller 212. In certain embodiments, tuning of the laser waveguide is performed by changing the temperature of an optical grating in the laser waveguide 204 which changes the frequency that is being emitted by the semiconductor device.

When using the tunable diode laser spectroscopy (TDLS), a common problem for long term stability is the emission wavelength drift from the diode laser. For example, the measurement accuracy is compromised without the correction of the drift. A widely used method to line-lock the TDL and avoid drift is to install a separate wavelength standard in the optical path. For example, an etalone or a reference gas cell, which provides a wavelength modulation that is stable enough to measure the drift from the diode laser, can be installed as a separate wavelength standard in the optical path. The measurement result can either be feedback to the laser control to compensate the drift, or input to the spectroscopy processing to correct the x axis shift in the spectrum. However, the separate optical path with the wavelength standard complicates the system, decreases the robustness, and increases the cost of the system.

Figure 9:
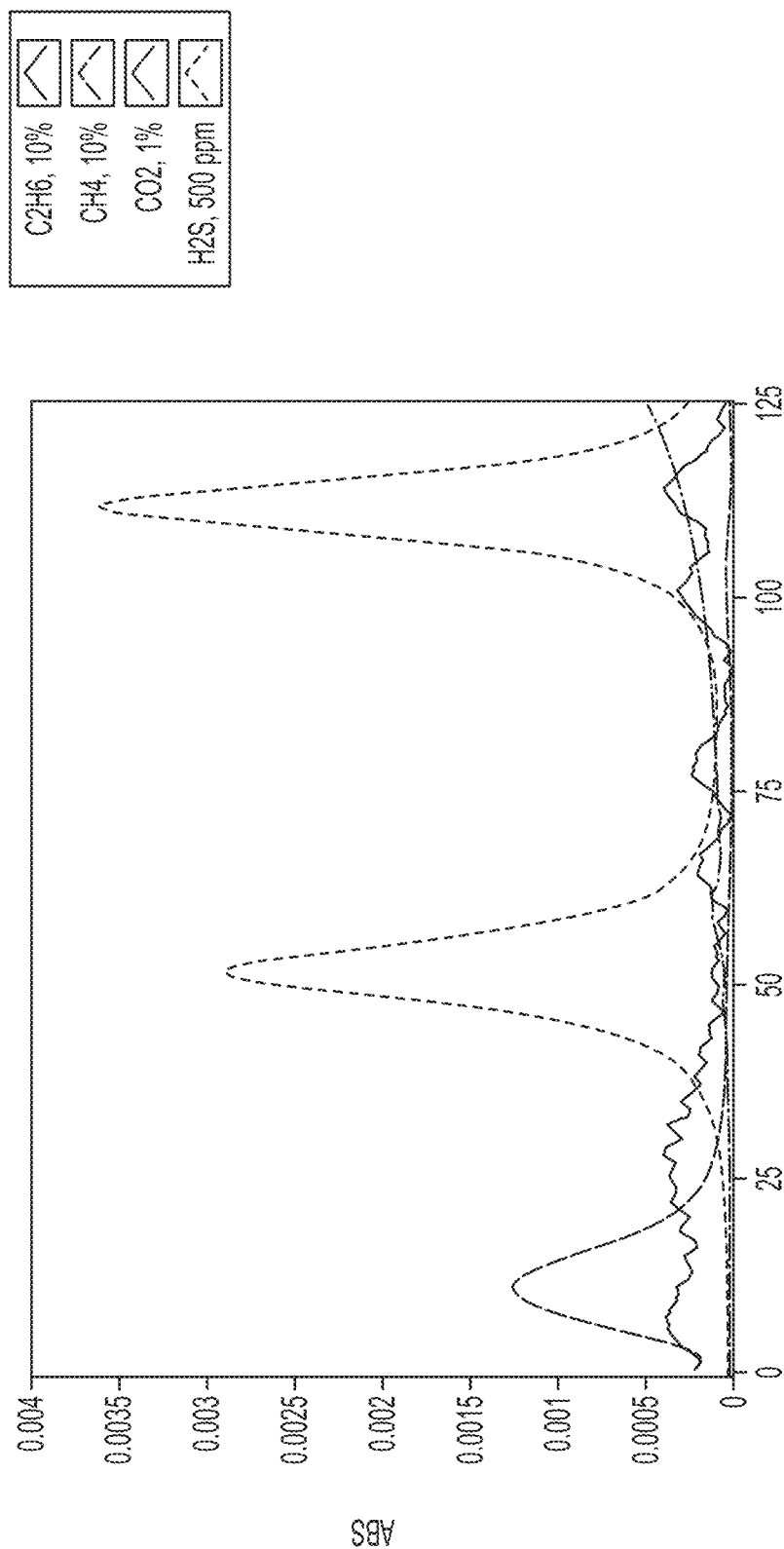
FIG. 9 is a plot of absorption features within a tuning range of the laser, according to an illustrative embodiment.

To avoid the drawbacks caused by adding a separate optical path with a wavelength standard to the system, a methane absorption peak was used to line-lock (or frequency load lock) the emission of a DFB-TDL for measuring $H_2S$ in natural gas background (FIG. 9). Such a system that uses a different background spectrum as a parasitical way to line-lock is not common in laser-based spectroscopy for natural gas, for example.

FIG. 9 shows an example of absorption features within the tuning range of the laser. The red curve is the methane absorption peak. The two blue peaks are the selected absorption features used for $H_2S$ measurement. The y axis is in the unit of absorbance. The x axis is wavelength in a unit related to the laser tuning position. If the emission of the TDL is stable, the red peak centers at about 10, and the two blue peaks center about 52 and 108, respectively. When the laser drifts, the relationship between the actual emission wavelength and the laser tuning position changes. Laser drift causes peak positions to shift from where the peak positions are expected to be, thereby causing errors in spectrum processing. As described herein, the red peak of FIG. 9 is from methane, which exists in the natural gas background. In the provided system, the laser pump current was varied to compensate for any drift from the laser, and lock the red peak to be at a value of about 10 at all times. Therefore, the $H_2S$ peaks can be line-locked (or frequency load locked) at about 52 and about 108. This setup reduces noise.

In this application, including the definitions below, the term 'module' or the term 'controller' may be replaced with the term 'circuit.' The term 'module' may refer to, be part of, or include: an Application Specific Integrated Circuit (ASIC); a digital, analog, or mixed analog/digital discrete circuit; a digital, analog, or mixed analog/digital integrated circuit; a combinational logic circuit; a field programmable gate array (FPGA); a processor circuit (shared, dedicated, or group) that executes code; a memory circuit (shared, dedicated, or group) that stores code executed by the processor circuit; other suitable hardware components that provide the described functionality; or a combination of some or all of the above, such as in a system-on-chip.

The term code, as used above, may include software, firmware, and/or microcode, and may refer to programs, routines, functions, classes, data structures, and/or objects. The term shared processor circuit encompasses a single processor circuit that executes some or all code from multiple modules. The term group processor circuit encompasses a processor circuit that, in combination with additional processor circuits, executes some or all code from one or more modules. References to multiple processor circuits encompass multiple processor circuits on discrete dies, multiple processor circuits on a single die, multiple cores of a single processor circuit, multiple threads of a single processor circuit, or a combination of the above. The term shared memory circuit encompasses a single memory circuit that stores some or all code from multiple modules. The term group memory circuit encompasses a memory circuit that, in combination with additional memories, stores some or all code from one or more modules.

The term memory circuit is a subset of the term computer-readable medium. The term computer-readable medium, as used herein, does not encompass transitory electrical or electromagnetic signals propagating through a medium (such as on a carrier wave); the term computer-readable medium may therefore be considered tangible and non-transitory. Non-limiting examples of a non-transitory, tangible computer-readable medium are nonvolatile memory circuits (such as a flash memory circuit, an erasable programmable read-only memory circuit, or a mask read-only memory circuit), volatile memory circuits (such as a static random access memory circuit or a dynamic random access memory circuit), magnetic storage media (such as an analog or digital magnetic tape or a hard disk drive), and optical storage media (such as a CD, a DVD, or a Blu-ray Disc).

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Figure 10:
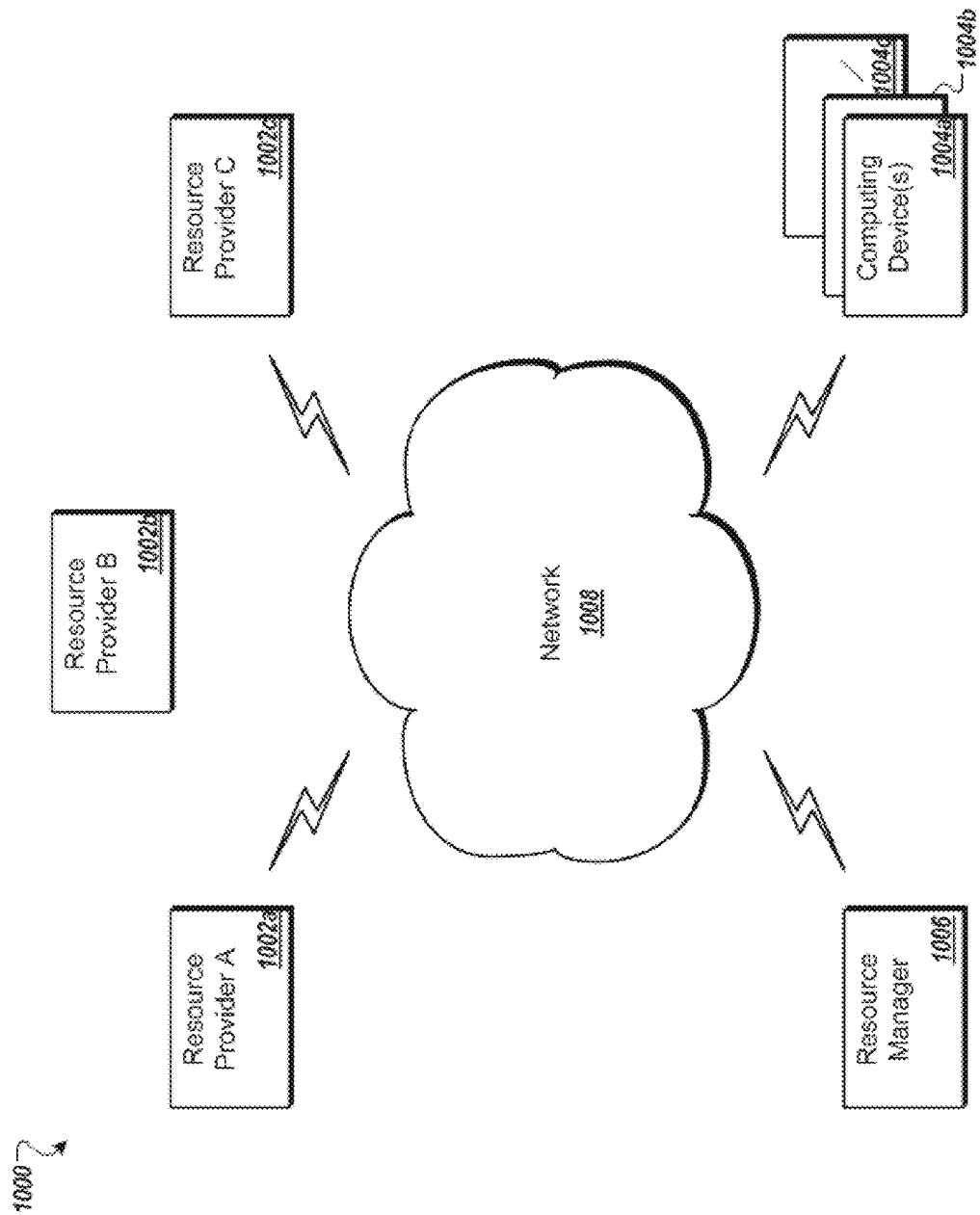
FIG. 10 is a block diagram of an example network environment for use with or in the system described herein, according to an illustrative embodiment.

FIG. 10 shows an illustrative network environment 1000 for use in the systems described herein. In brief overview, referring now to FIG. 10, a block diagram of an exemplary cloud computing environment 1000 is shown and described.

The cloud computing environment 1000 may include one or more resource providers 1002a, 1002b, 1002c (collectively, 1002). Each resource provider 1002 may include computing resources. In some implementations, computing resources may include any hardware and/or software used to process data. For example, computing resources may include hardware and/or software capable of executing algorithms, computer programs, and/or computer applications. In some implementations, exemplary computing resources may include application servers and/or databases with storage and retrieval capabilities. Each resource provider 1002 may be connected to any other resource provider 1002 in the cloud computing environment 1000. In some implementations, the resource providers 1002 may be connected over a computer network 1008. Each resource provider 1002 may be connected to one or more computing device 1004a, 1004b, 1004c (collectively, 1004), over the computer network 1008.

The cloud computing environment 1000 may include a resource manager 1006. The resource manager 1006 may be connected to the resource providers 1002 and the computing devices 1004 over the computer network 1008. In some implementations, the resource manager 1006 may facilitate the provision of computing resources by one or more resource providers 1002 to one or more computing devices 1004. The resource manager 1006 may receive a request for a computing resource from a particular computing device 1004. The resource manager 1006 may identify one or more resource providers 1002 capable of providing the computing resource requested by the computing device 1004. The resource manager 1006 may select a resource provider 1002 to provide the computing resource. The resource manager 1006 may facilitate a connection between the resource provider 1002 and a particular computing device 1004. In some implementations, the resource manager 1006 may establish a connection between a particular resource provider 1002 and a particular computing device 1004. In some implementations, the resource manager 1006 may redirect a particular computing device 1004 to a particular resource provider 1002 with the requested computing resource.

Figure 11:
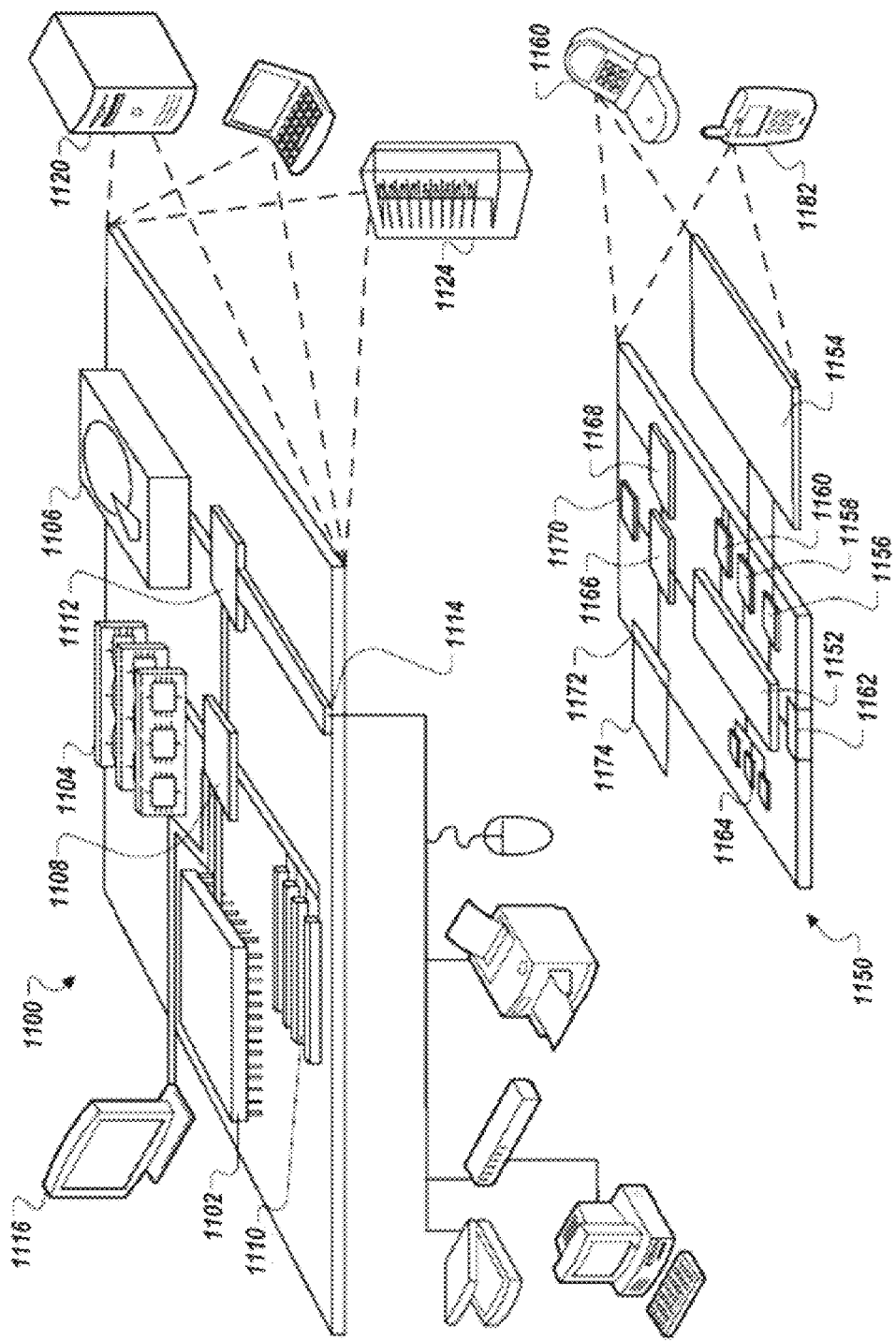
FIG. 11 is a block diagram of an example computing device and an example mobile computing device, for use in illustrative embodiments.
Figure 12:
FIG. 12 is a schematic of a spectroscopy system, according to an illustrative embodiment.
Figure 13:
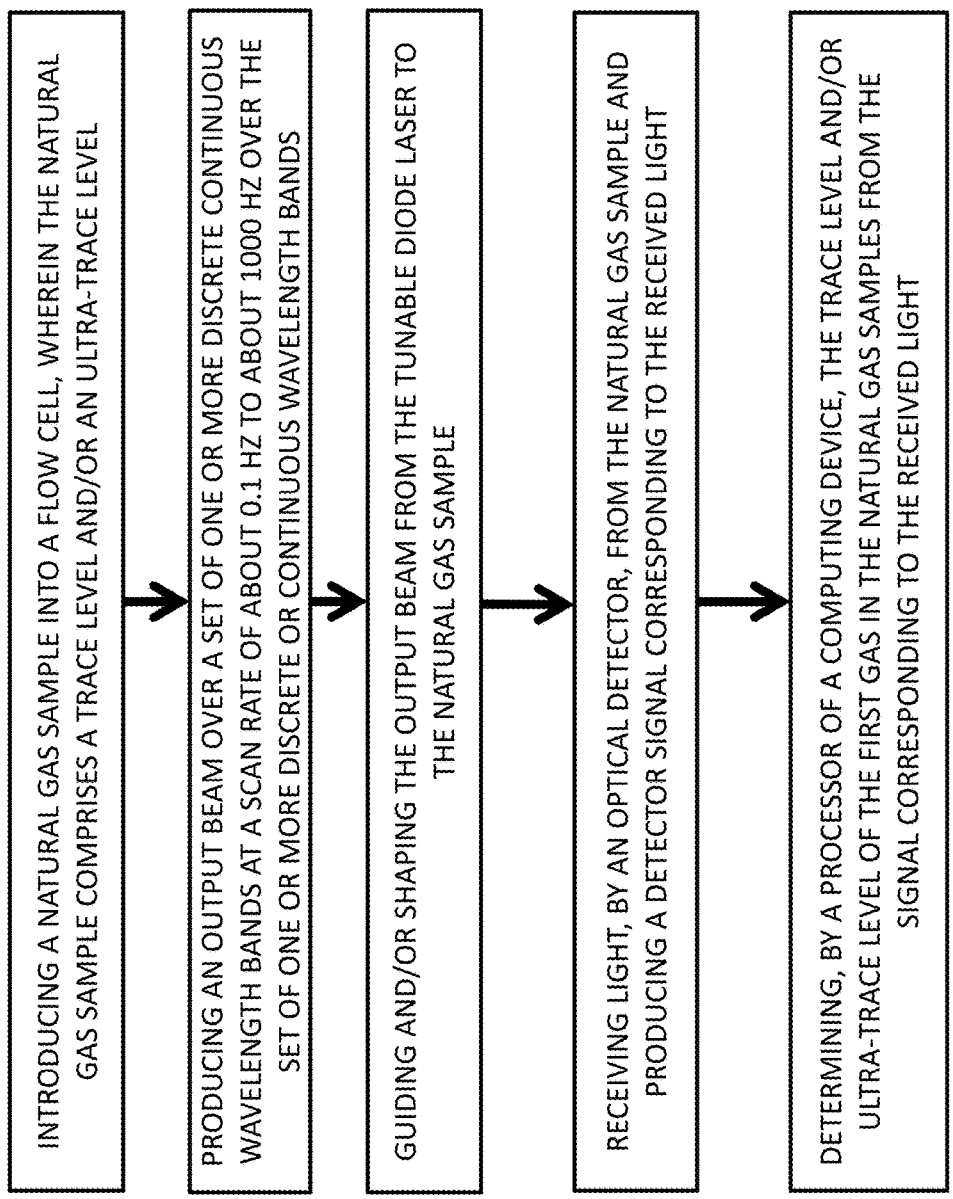
FIG. 13 is a schematic of a spectroscopy method, according to an illustrative embodiment.

FIG. 11 shows an example of a computing device 1100 and a mobile computing device 1150 that can be used in the methods and systems described in this disclosure. The computing device 1100 is intended to represent various forms of digital computers, such as laptops, desktops, workstations, personal digital assistants, servers, blade servers, mainframes, and other appropriate computers. The mobile computing device 1150 is intended to represent various forms of mobile devices, such as personal digital assistants, cellular telephones, smart-phones, and other similar computing devices. The components shown here, their connections and relationships, and their functions, are meant to be examples only, and are not meant to be limiting.

The computing device 1100 includes a processor 1102, a memory 1104, a storage device 1106, a high-speed interface 1108 connecting to the memory 1104 and multiple high-speed expansion ports 1110, and a low-speed interface 1112 connecting to a low-speed expansion port 1114 and the storage device 1106. Each of the processor 1102, the memory 1104, the storage device 1106, the high-speed interface 1108, the high-speed expansion ports 1110, and the low-speed interface 1112, are interconnected using various busses, and may be mounted on a common motherboard or in other manners as appropriate. The processor 1102 can process instructions for execution within the computing device 1100, including instructions stored in the memory 1104 or on the storage device 1106 to display graphical information for a GUI on an external input/output device, such as a display 1116 coupled to the high-speed interface 1108. In other implementations, multiple processors and/or multiple buses may be used, as appropriate, along with multiple memories and types of memory. Also, multiple computing devices may be connected, with each device providing portions of the necessary operations (e.g., as a server bank, a group of blade servers, or a multi-processor system).

The memory 1104 stores information within the computing device 1100. In some implementations, the memory 1104 is a volatile memory unit or units. In some implementations, the memory 1104 is a non-volatile memory unit or units. The memory 1104 may also be another form of computer-readable medium, such as a magnetic or optical disk.

The storage device 1106 is capable of providing mass storage for the computing device 1100. In some implementations, the storage device 1106 may be or contain a computer-readable medium, such as a floppy disk device, a hard disk device, an optical disk device, or a tape device, a flash memory or other similar solid state memory device, or an array of devices, including devices in a storage area network or other configurations. Instructions can be stored in an information carrier. The instructions, when executed by one or more processing devices (for example, processor 1102), perform one or more methods, such as those described above. The instructions can also be stored by one or more storage devices such as computer- or machine-readable mediums (for example, the memory 1104, the storage device 1106, or memory on the processor 1102).

The high-speed interface 1108 manages bandwidth-intensive operations for the computing device 1100, while the low-speed interface 1112 manages lower bandwidth-intensive operations. Such allocation of functions is an example only. In some implementations, the high-speed interface 1108 is coupled to the memory 1104, the display 1116 (e.g., through a graphics processor or accelerator), and to the high-speed expansion ports 1110, which may accept various expansion cards (not shown). In the implementation, the low-speed interface 1112 is coupled to the storage device 1106 and the low-speed expansion port 1114. The low-speed expansion port 1114, which may include various communication ports (e.g., USB, Bluetooth®, Ethernet, wireless Ethernet) may be coupled to one or more input/output devices, such as a keyboard, a pointing device, a scanner, or a networking device such as a switch or router, e.g., through a network adapter.

The computing device 1100 may be implemented in a number of different forms, as shown in the figure. For example, it may be implemented as a standard server 1120, or multiple times in a group of such servers. In addition, it may be implemented in a personal computer such as a laptop computer 1122. It may also be implemented as part of a rack server system 1124. Alternatively, components from the computing device 1100 may be combined with other components in a mobile device (not shown), such as a mobile computing device 1150. Each of such devices may contain one or more of the computing device 1100 and the mobile computing device 1150, and an entire system may be made up of multiple computing devices communicating with each other.

The mobile computing device 1150 includes a processor 1152, a memory 1164, an input/output device such as a display 1154, a communication interface 1166, and a transceiver 1168, among other components. The mobile computing device 1150 may also be provided with a storage device, such as a micro-drive or other device, to provide additional storage. Each of the processor 1152, the memory 1164, the display 1154, the communication interface 1166, and the transceiver 1168, are interconnected using various buses, and several of the components may be mounted on a common motherboard or in other manners as appropriate.

The processor 1152 can execute instructions within the mobile computing device 1150, including instructions stored in the memory 1164. The processor 1152 may be implemented as a chipset of chips that include separate and multiple analog and digital processors. The processor 1152 may provide, for example, for coordination of the other components of the mobile computing device 1150, such as control of user interfaces, applications run by the mobile computing device 1150, and wireless communication by the mobile computing device 1150.

The processor 1152 may communicate with a user through a control interface 1158 and a display interface 1156 coupled to the display 1154. The display 1154 may be, for example, a TFT (Thin-Film-Transistor Liquid Crystal Display) display or an OLED (Organic Light Emitting Diode) display, or other appropriate display technology. The display interface 1156 may comprise appropriate circuitry for driving the display 1154 to present graphical and other information to a user. The control interface 1158 may receive commands from a user and convert them for submission to the processor 1152. In addition, an external interface 1162 may provide communication with the processor 1152, so as to enable near area communication of the mobile computing device 1150 with other devices. The external interface 1162 may provide, for example, for wired communication in some implementations, or for wireless communication in other implementations, and multiple interfaces may also be used.

The memory 1164 stores information within the mobile computing device 1150. The memory 1164 can be implemented as one or more of a computer-readable medium or media, a volatile memory unit or units, or a non-volatile memory unit or units. An expansion memory 1174 may also be provided and connected to the mobile computing device 1150 through an expansion interface 1172, which may include, for example, a SIMM (Single In Line Memory Module) card interface. The expansion memory 1174 may provide extra storage space for the mobile computing device 1150, or may also store applications or other information for the mobile computing device 1150. Specifically, the expansion memory 1174 may include instructions to carry out or supplement the processes described above, and may include secure information also. Thus, for example, the expansion memory 1174 may be provided as a security module for the mobile computing device 1150, and may be programmed with instructions that permit secure use of the mobile computing device 1150. In addition, secure applications may be provided via the SIMM cards, along with additional information, such as placing identifying information on the SIMM card in a non-hackable manner.

The memory may include, for example, flash memory and/or NVRAM memory (non-volatile random access memory), as discussed below. In some implementations, instructions are stored in an information carrier and, when executed by one or more processing devices (for example, processor 1152), perform one or more methods, such as those described above. The instructions can also be stored by one or more storage devices, such as one or more computer- or machine-readable mediums (for example, the memory 1164, the expansion memory 1174, or memory on the processor 1152). In some implementations, the instructions can be received in a propagated signal, for example, over the transceiver 1168 or the external interface 1162.

The mobile computing device 1150 may communicate wirelessly through the communication interface 1166, which may include digital signal processing circuitry where necessary. The communication interface 1166 may provide for communications under various modes or protocols, such as GSM voice calls (Global System for Mobile communications), SMS (Short Message Service), EMS (Enhanced Messaging Service), or MMS messaging (Multimedia Messaging Service), CDMA (code division multiple access), TDMA (time division multiple access), PDC (Personal Digital Cellular), WCDMA (Wideband Code Division Multiple Access), CDMA2000, or GPRS (General Packet Radio Service), among others. Such communication may occur, for example, through the transceiver 1168 using a radio-frequency. In addition, short-range communication may occur, such as using a Bluetooth®, Wi-Fi™, or other such transceiver (not shown). In addition, a GPS (Global Positioning System) receiver module 1170 may provide additional navigation- and location-related wireless data to the mobile computing device 1150, which may be used as appropriate by applications running on the mobile computing device 1150.

The mobile computing device 1150 may also communicate audibly using an audio codec 1160, which may receive spoken information from a user and convert it to usable digital information. The audio codec 1160 may likewise generate audible sound for a user, such as through a speaker, e.g., in a handset of the mobile computing device 1150. Such sound may include sound from voice telephone calls, may include recorded sound (e.g., voice messages, music files, etc.) and may also include sound generated by applications operating on the mobile computing device 1150.

The mobile computing device 1150 may be implemented in a number of different forms, as shown in the figure. For example, it may be implemented as a cellular telephone 1180. It may also be implemented as part of a smart-phone 1182, personal digital assistant, or other similar mobile device.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms machine-readable medium and computer-readable medium refer to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term machine-readable signal refers to any signal used to provide machine instructions and/or data to a programmable processor.

To provide for interaction with a user, the systems and techniques described here can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described here can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network (LAN), a wide area network (WAN), and the Internet.

The computing system can include clients and servers. A client and server are generally remote from each other and typically interact through a communication network. The relationship of client and server arises by virtue of computer programs running on the respective computers and having a client-server relationship to each other.

While the description includes specific embodiments, it should be understood by those skilled in the art that various changes in form and detail may be made therein without departing from the spirit and scope of the invention as defined by the appended claims.

EQUIVALENTS

While the invention has been particularly shown and described with reference to specific preferred embodiments, it should be understood by those skilled in the art that various changes in form and detail may be made therein without departing from the spirit and scope of the invention as defined by the appended claims. The relevant teachings of all the references, patents and patent applications cited herein are incorporated herein by reference in their entirety.

What is claimed is:

1. A spectroscopy system for measuring a trace level and/or an ultra-trace level of a gas in a natural gas sample, the system comprising:
    a laser for producing an output beam over a set of one or more discrete or continuous wavelength bands at a scan rate from about 0.1 Hz to about 1000 Hz over the set of one or more discrete or continuous wavelength bands;
    transmitting optics for guiding and/or shaping the output beam from the laser to the natural gas sample;
    an optical detector for receiving light from the natural gas sample and producing a detector signal corresponding to the received light; and
    a processor of a computing device and a memory having instructions stored thereon, wherein the instructions, when executed by the processor, cause the processor to compute the trace level and/or ultra-trace level of the gas in the natural gas sample from the signal corresponding to the received light, wherein the gas is hydrogen sulfide and wherein the set of one or more discrete or continuous wavelength bands comprises one or both of bands (i) and (ii) as follows:
(i) a first band at least 0.05 $cm^{-1}$ in width, said first band containing at least one value between 5066 $cm^{-1}$ and 5076 $cm^{-1}$; and
(ii) a second band at least 0.05 $cm^{-1}$ in width, said second band containing at least one value between 5086 $cm^{-1}$ and 5097 $cm^{-1}$.

2. The system of claim 1, wherein the instructions, when executed by the processor, cause the processor to synchronize wavelength scanning of the laser with the detector signal to align, in a time domain, measurement of the detector signal with the wavelength scanning to generate an absorption spectrum.

3. The system of claim 2, wherein the instructions, when executed by the processor, cause the processor to analyze the generated absorption to determine the trace level and/or ultra-trace level of the gas in the natural gas sample.

4. The system of claim 1, wherein the natural gas sample is at least 20% methane and/or an ultra-trace amount.

5. The system of claim 1, wherein the instructions, when executed by the processor, identify an absorption peak corresponding to methane in the natural gas sample and use the absorption peak corresponding to methane to line-lock output wavelength of the laser and stabilize one or more output wavelength bands of the laser, thereby reducing error caused by laser drift without use of a separate reference gas cell.

6. The system of claim 1, further comprising a supplemental optical detector for receiving light from the output beam of the laser that does not pass through the natural gas sample, and for producing a resulting supplemental signal, wherein the instructions, when executed by the processor, analyze the supplemental signal to determine a reference channel baseline signature and subtract the reference channel baseline signature from a sample gas baseline signal, thereby reducing noise.

7. The system of claim 1, further comprising a sample gas conditioning system.

8. The system of claim 1, further comprising a flow control device for controlling a flow rate of the natural gas sample into/through the flow cell.

9. The system of claim 1, further comprising a pump for controlling and/or reducing pressure of the natural gas sample prior to flow of the sample into/through the flow cell.

10. The system of claim 1, further comprising a vacuum pump for producing a vacuum of the natural gas sample in the flow cell.

11. The system of claim 1, wherein the laser comprises a member selected from the group consisting of:
a tunable diode laser,
an external cavity diode laser or a vertical external-cavity surface-emitting laser (VECSEL), and
a tunable quantum cascade laser (QCL).

12. A spectroscopy method for measuring a trace level and/or an ultra-trace level of a gas in a natural gas sample, the method comprising:
producing an output beam from a laser over a set of one or more discrete or continuous wavelength bands at a scan rate from about 0.1 Hz to about 1000 Hz over the set of one or more discrete or continuous wavelength bands;

introducing a natural gas sample into a flow cell, wherein the natural gas sample comprises a trace level and/or an ultra-trace level;
guiding and/or shaping the output beam from the laser to the natural gas sample;
receiving light, by an optical detector, from the natural gas sample and producing a detector signal corresponding to the received light; and
determining, by a processor of a computing device and a memory having instructions stored thereon, the trace level and/or ultra-trace level of the gas in the natural gas sample from the signal corresponding to the received light,
wherein the gas is hydrogen sulfide and wherein the set of one or more discrete or continuous wavelength bands comprises one or both of bands (i) and (ii) as follows:
(i) a first band at least 0.05 $cm^{-1}$ in width, said first band containing at least one value between 5066 $cm^{-1}$ and 5076 $cm^{-1}$; and
(ii) a second band at least 0.05 $cm^{-1}$ in, said second band containing at least one value between 5086 $cm^{-1}$ and 5097 $cm^{-1}$.

13. The method of claim 12, further comprising:
synchronizing, by the processor, wavelength scanning of the laser with the detector signal to align, in a time domain, measurement of the detector signal with the wavelength scanning to generate an absorption spectrum.

14. The method of claim 13, further comprising:
analyzing, by the processor, the generated absorption spectrum to determine the trace level and/or ultra-trace level of the gas in the natural gas sample.

15. The method of claim 14, further comprising:
performing a chemometric analysis of the generated absorption spectrum either in the time domain or frequency domain.

16. The method of claim 12, wherein the natural gas sample is at least 20% methane.

17. The method of claim 12, further comprising:
identifying, by the processor, an absorption peak corresponding to methane in the natural gas sample; and
using the absorption peak corresponding to methane to line-lock, by the processor, output wavelength of the laser and stabilize one or more output wavelength bands of the laser, thereby reducing error caused by laser drift without use of a separate reference gas cell.

18. The method of claim 12, further comprising:
receiving light from the output beam of the laser that does not pass through the natural gas sample;
producing a resulting supplemental signal; and
analyzing, by the processor, the supplemental signal to determine a reference channel baseline signature and subtracting the reference channel baseline signature from a sample gas baseline signal, thereby reducing noise.

19. The method of claim 12, further comprising:
conditioning the natural gas sample.

20. The method of claim 12, further comprising
controlling a flow rate of the natural gas sample into/through the flow cell.

21. The method of claim 12, further comprising
controlling and/or reducing pressure of the natural gas sample prior to flow of the sample into/through the flow cell.

22. The method of claim 12, further comprising
producing a vacuum of the natural gas sample in the flow cell.

23. The method of claim 12, wherein the laser comprises a member selected from the group consisting of:
a tunable diode laser,
an external cavity diode laser or a vertical external-cavity surface-emitting laser (VECSEL), and
a tunable quantum cascade laser (QCL).

24. A system for measuring hydrogen sulfide in natural gas, comprising:
a light source emitting light at a frequency substantially corresponding to an absorption line of hydrogen sulfide in the 5066-5076 $cm^{-1}$ (1970-1974 nm) wavelength range or 5086-5097 $cm^{-1}$ (1962-1966 nm) wavelength range, wherein the light source is positioned to emit light through the natural gas, the light source scans over the wavelength range at a rate from 10 Hz to 200 Hz;
a first detector configured to detect an intensity of the light emitted from the light source;
a second detector configure to detect an intensity of the light after passing through the natural gas, the signals from the detectors are sampled with a resolution from 0.01 to 0.0001 $cm^{-1}$; and
a processing device coupled to the first and second detector for determining the level of hydrogen sulfide in the natural gas.

* * * * *